United States Patent
Ziegler

(10) Patent No.: US 6,319,925 B1
(45) Date of Patent: Nov. 20, 2001

(54) O-BENZYL OXIME ETHER DERIVATIVES AND THEIR USE IN CROP PROTECTION COMPOSITIONS

(75) Inventor: Hugo Ziegler, Witterswil (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 08/981,573

(22) PCT Filed: Jun. 14, 1996

(86) PCT No.: PCT/EP96/02569

§ 371 Date: Dec. 22, 1997

§ 102(e) Date: Dec. 22, 1997

(87) PCT Pub. No.: WO97/01530

PCT Pub. Date: Jan. 16, 1997

(30) Foreign Application Priority Data

Jun. 27, 1995 (CH) .................................. 1878/95
May 14, 1996 (CH) .................................. 1225/96

(51) Int. Cl.[7] .......................... A01N 37/18; A01N 37/44; A01N 43/16; A01N 43/58

(52) U.S. Cl. ..................... 514/249; 514/255; 514/274; 514/312; 514/367; 514/459; 514/538; 514/539; 514/620; 544/235; 544/335; 544/336; 546/153; 546/157; 546/335; 548/170; 549/77; 560/35; 564/134; 564/139; 564/142; 564/163; 564/164

(58) Field of Search ................... 514/249, 255, 514/274, 312, 367, 459, 538, 539, 620; 544/235, 335, 336; 546/335, 153, 157; 548/170; 549/77; 560/35; 564/134, 139, 142, 163, 164

(56) References Cited

U.S. PATENT DOCUMENTS

| | | | |
|---|---|---|---|
| 5,874,467 | 2/1999 | Bayer et al. ............... | 514/538 |
| 5,889,059 | 3/1999 | Bayer et al. ............... | 514/619 |
| 5,981,581 | 11/1999 | Bayer et al. ............... | 514/522 |
| 5,990,339 | 11/1999 | Bayer et al. ............... | 558/436 |
| 6,066,756 | 5/2000 | Bayer et al. ............... | 558/440 |
| 6,100,263 | 8/2000 | Bayer et al. ............... | 514/241 |
| 6,127,568 | 10/2000 | Bayer et al. ............... | 558/414 |
| 6,187,812 | 2/2001 | Bayer et al. ............... | 514/522 |

FOREIGN PATENT DOCUMENTS

| | | |
|---|---|---|
| 0 414 153 | 2/1991 | (EP) . |
| 0 566 455 | 10/1993 | (EP) . |
| 90 07493 | 7/1990 | (WO) . |
| 95 21153 | 8/1995 | (WO) . |
| 97/01530 | 1/1997 | (WO) . |
| 95 21154 | 8/1998 | (WO) . |

Primary Examiner—Peter O'Sullivan
(74) Attorney, Agent, or Firm—Joseph C. Gil

(57) ABSTRACT

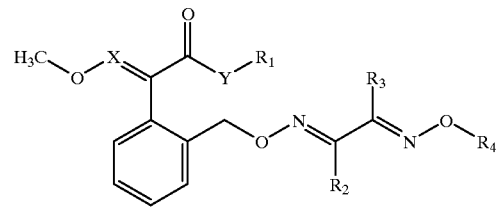

(I)

Oxime ethers of formula (I) in which a) X is an N atom and Y is an oxygen atom or NH, or b) X is CH and Y is an oxygen atom, in which furthermore $R_1$ is $C_1$–$C_4$alkyl; $R_2$ is hydrogen, $C_1$–$C_4$alkyl or cyclopropyl; and in which $R_3$ and $R_4$ are as defined herein, are fungicidal, acaricidal and insecticidal active ingredients for agriculture. They can be employed as formulated crop protection compositions.

29 Claims, No Drawings

O-BENZYL OXIME ETHER DERIVATIVES AND THEIR USE IN CROP PROTECTION COMPOSITIONS

The present invention relates to oxime ethers of the general formula I

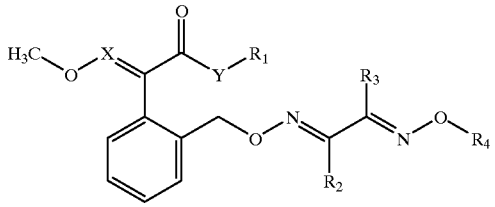

and their possible isomers and isomer mixtures, in which
a)
X is an N atom and
Y is an oxygen atom or NH, or
b)
X is CH and
Y is an oxygen atom,
in which furthermore
$R_1$ is $C_1$–$C_4$alkyl;
$R_2$ is hydrogen, $C_1$–$C_4$alkyl or cyclopropyl;
$R_3$ is $C_1$–$C_6$alkoxy which is unsubstituted or substituted by 1 to 5 halogen atoms, substituted or unsubstituted aryloxy, $C_1$–$C_6$alkylthio which is unsubstituted or substituted by 1 to 5 halogen atoms, substituted or unsubstituted arylthio, substituted or unsubstituted heteroaryloxy, substituted or unsubstituted heteroarylthio, substituted or unsubstituted aralkyl, substituted or unsubstituted biphenyl, substituted or unsubstituted $C_2$–$C_4$alkynylphenyl, substituted or unsubstituted heteroarylmethyl; and
$R_4$ is $C_1$–$C_6$alkyl; $C_1$–$C_6$haloalkyl having 1 to 5 halogen atoms; $C_1$–$C_4$alkoxy-$C_1$–$C_2$alkyl; $C_2$–$C_6$alkenyl which is unsubstituted or substituted by 1 to 3 halogen atoms; $C_2$–$C_6$alkynyl; $C_3$–$C_6$cycloalkyl-$C_1$–$C_4$alkyl which is unsubstituted or substituted by 1 to 4 halogen atoms;
where $R_3$ has a meaning other than dichlorobenzyl when, simultaneously, $R_1$ is methyl, $R_2$ is hydrogen, X is CH, Y is oxygen and $R_4$ is $C_1$–$C_4$alkyl.

The compounds according to the invention have microbicidal, acaricidal and insecticidal. properties and are suitable as agrochemical active ingredients for use in agriculture.

The invention furthermore relates to a process for the preparation of the compounds according to the invention, and to fungicidal, acaricidal and insecticidal compositions which contain such compounds as active ingredients, and to the use of such compounds and compositions for the control of phytopathogenic fungi, Acarina and insects and for the prevention of such an attack.

If asymmetric carbon atoms are present in the compounds of the formula I, the compounds occur in optically active form. Solely on the basis of the presence of the aliphatic and the oximino double bonds, the compounds in each case occur in [E] and/or [Z] forms. Atropisomerism can furthermore occur. The formula I is intended to include all these possible isomeric forms as well as their mixtures, e.g. racemic mixtures and any desired [E/Z] mixtures.

Depending on the number of carbon atoms, alkyl and alkoxy groups are straight-chain or branched. The alkyl radical in these groups is, for example, methyl, ethyl, n-propyl, isopropyl, n-butyl, sec-butyl, isobutyl, tert-butyl, n-pentyl, neopentyl, sec-pentyl, tert-pentyl, n-hexyl etc.

Cycloalkyl is to be understood as meaning cyclopropyl, cyclobutyl, cyclopentyl or cyclohexyl.

Alkenyl is to be understood as meaning straight-chain or branched alkenyl, e.g. vinyl, 1-methylvinyl, allyl, 1-butenyl, isopropenyl.

Alkynyl is, for example, ethynyl, 1-propynyl or 1-butynyl. $C_2$–$C_4$alkynylphenyl is alkynyl bound to the residual molecule via a phenyl group. $C_4$alkynylphenyl includes 1,3-butadi-1-ynylphenyl.

Halogen is fluorine, chlorine, bromine or iodine, preferably fluorine, chlorine or bromine.

Haloalkyl can contain identical or different halogen atoms.

Substituents of the aryloxy, arylthio, heteroaryloxy, heteroarylthio, aralkyl, heteroarylmethyl, biphenyl and $C_2$–$C_4$alkynylphenyl groups which, where appropriate, are substituted are, inter alia. $C_1$–$C_4$alkyl, $C_1$–$C_4$alkoxy, $C_1$–$C_4$haloalkyl (especially $CF_3$), $C_1$–$C_4$haloalkoxy (especially $OCF_3$), $C_1$–$C_4$akylthio, halogen, nitro, cyano, $C_1$–$C_4$alkylsulfinyl, $C_1$–$C_4$alkylsulfonyl. Further substituents, especially on the alkynyl radical of the substituted or unsubstituted $C_2$–$C_4$alkynylphenyl group, are furthermore substituted or unsubstituted phenyl, pyridoyl or benzoyl (where the substituents on these six-membered rings can be $C_1$–$C_4$alkyl, $C_1$–$C_4$alkoxy, $C_1$–$C_4$haloalkyl (especially $CF_3$), $C_1$–$C_4$haloalkoxy (especially $OCF_3$), $C_1$–$C_4$alkylthio, halogen, nitro, cyano, $C_1$–$C_4$alkylsulfinyl, $C_1$–$C_4$alkylsulfonyl), furthermore free or $C_1$–$C_4$acylated or O—$C_1$–$C_4$alkylated $C_1$–$C_4$hydroxyalkyl, $C_1$–$C_5$alkoxycarbonyl; N,N-di($C_1$–$C_4$alkyl)carbamoyl; N-$C_1$–$C_4$alkyl-N-$C_1$–$C_4$alkoxycarbamoyl; unsubstituted or halogen-substituted cyclopropyloxycarbonyl or $C_2$–$C_5$alkenyl, which is unsubstituted or substituted by $C_2$–$C_4$alkoxy and/or halogen; furthermore five- or six-membered heteroaryl which can be unsubstituted or substituted by one or more of the substituents halogen, cyano, hydroxyl and also alkyl, alkenyl, alkoxy, alkenyloxy or alkynyloxy each having up to 4 carbon atoms.

The substituents can independently of one another be present 1 to 3 times.

Aryl is phenyl or naphthyl, preferably phenyl.

The term heteroaryl includes, inter alia, five- and six-membered aromatic rings having 1–3 identical or different heteroatoms N, O or S, to which, if desired, a benzo ring can be fused. Examples are pyridine, pyrimidine, pyrazine, pyridazine, triazine, quinoline, isoquinoline, quinazoline, quinoxaline, benzothiazole, benzoxazole, 1-methylimidazole, 1-methyltetrazole, 4-methyl-1,2,4-triazole.

In EP-A-0 414 153 and in WO-A-90/07493 similar compounds have been disclosed useful as fungicides. The instant compounds of formula I are useful as fungicides and insecticides. The presence of a double oxime side chain in the structural pattern exhibits improved stability to the molecule.

An important subgroup of compounds are those of the formula I, in which
$R_3$ is $C_1$–$C_6$alkoxy; $C_1$–$C_4$haloalkoxy; substituted or unsubstituted phenoxy; $C_1$–$C_6$alkylthio which is unsubstituted or substituted by 1 to 3 substituents selected from halogen, $C_1$–$C_4$alkyl, $C_1$–$C_4$alkoxy, $CF_3$ and substituted phenylthio; or is unsubstituted or in each case halo-substituted pyridyloxy, pyrimidinyloxy, quinolyloxy, quinazolinyloxy or quinoxazolinyl; or an unsubstituted or $C_1$–$C_4$alkyl- or halogen-substituted benzothiazolylthio, benzoxazolylthio, imidazolylthio or tetrazolylthio radical; or a diphenyl, $C_2$–$C_4$alkynylphenyl, benzyl or naphthylmethyl, which is unsubstituted or substituted by 1 to 3 substituents selected from halogen, $C_1$–$C_4$alkyl, $C_1$–$C_4$alkoxy, $CF_3$ and CN;

$R_4$ is $C_1$–$C_4$alkyl; $C_1$–$C_4$haloalkyl; unsubstituted or halo-substituted $C_2$–$C_4$alkenyl; $C_3$–$C_4$alkynyl; unsubstituted or halo-substituted cyclopropylmethyl; while X, Y, $R_1$ and $R_2$ are as defined for formula I.

Among the last-mentioned compounds, those are preferred in which $R_1$ is methyl and $R_2$ is hydrogen, methyl or cyclopropyl, while X, Y, $R_3$ and $R_4$ are as defined.

The following substituent combinations are preferred in the context of the invention:

1) Compounds of the formula I in which:
X is CH or N
Y is oxygen,
$R_1$ is methyl or ethyl
$R_2$ is methyl or cyclopropyl, and in which
$R_3$ and $R_4$ are as defined for formula I.

2) Compounds of the formula I in which:
X is N,
Y is NH,
$R_1$ is methyl, ethyl or isopropyl
$R_2$ is methyl or cyclopropyl, and in which
$R_3$ and $R_4$ are as defined for formula I.

3) Compounds of the formula I in which:
$R_1$ is methyl
$R_2$ is methyl
$R_4$ is $C_1$–$C_6$alkyl, while
X, Y and $R_3$ are as defined for formula I.

4) Compounds of the formula I in which:
$R_1$ is methyl
$R_2$ is methyl
$R_3$ is substituted or unsubstituted $C_1$–$C_6$alkoxy or substituted or unsubstituted
$C_1$–$C_6$alkylthio, while
X, Y and $R_4$ are as defined for formula I.

5) Compounds of the formula I in which:
$R_1$ is methyl
$R_2$ is methyl
$R_3$ is substituted or unsubstituted aryloxy or substituted or unsubstituted arylthio, while
X, Y and $R_4$ are as defined for formula I.

6) Compounds of the formula I in which:
$R_1$ is methyl
$R_2$ is methyl
$R_3$ is substituted or unsubstituted heteroaryloxy or substituted or unsubstituted heteroarylthio, while
X, Y and $R_4$ are as defined for formula I.

7) Compounds of the formula I in which:
$R_1$ is methyl
$R_2$ is methyl
$R_3$ is substituted or unsubstituted benzyl or substituted or unsubstituted heteroarylmethyl, while
X, Y and $R_4$ are as defined for formula I.

8) Compounds of the formula I in which:
$R_1$ is methyl
$R_2$ is methyl
$R_3$ is substituted or unsubstituted biphenyl or substituted or unsubstituted
$C_2$–$C_4$alkynylphenyl, while
X, Y and $R_4$ are as defined for formula I.

9) Within the last-mentioned subgroup 8), those compounds are preferred in which $R_4$ is methyl, ethyl or allyl, $R_3$ is an unsubstituted or substituted $C_2$–$C_4$alkynylphenyl group in which the possible substituent is located on the alkynyl group and is selected from $C_1$–$C_4$alkyl, $C_1$–$C_4$alkoxy, $C_1$–$C_4$haloalkyl (especially $CF_3$), $C_1$–$C_4$haloalkoxy (especially $OCF_3$), $C_1$–$C_4$alkylthio, halogen, nitro, cyano, $C_1$–$C_4$alkylsulfinyl, $C_1$–$C_4$alkylsulfonyl, unsubstituted or substituted phenyl (where the phenyl substituents are selected from $C_1$–$C_4$alkyl, $C_1$–$C_4$alkoxy, hydroxyl, $C_1$–$C_4$haloalkyl, $C_1$–$C_4$haloalkoxy, $C_1$–$C_4$alkylthio, halogen, nitro and cyano); $C_1$–$C_4$hydroxyalkyl, which can be O-acylated($C_1$–$C_4$) or O-alkylated($C_1$–$C_4$); $C_1$–$C_5$alkoxycarbonyl; carbamoyl; N-($C_1$–$C_4$alkyl) carbamoyl; N,N-di($C_1$–$C_4$alkyl)carbamoyl; N-$C_1$–$C_4$alkyl-N-$C_1$–$C_4$alkoxycarbamoyl; unsubstituted or halogen-substituted cyclopropylmethoxycarbonyl, unsubstituted, $C_1$–$C_4$alkoxy-substituted or halogen-substituted $C_2$–$C_5$alkenyl, and a five- or six-membered heteroaryl ring which is unsubstituted or substituted by halogen, cyano, hydroxyl, and also alkyl, alkenyl, alkoxy, alkenyloxy or alkynyloxy each having not more than 4 carbon atoms.

10) An important group among the compounds of subgroup 9) are those in which $R_3$ is an unsubstituted or substituted ethynylphenyl group, the possible substituent on the ethynyl group being selected from $C_1$–$C_4$alkyl; $C_1$–$C_4$alkoxy; $C_1$–$C_2$haloalkyl; $C_1$–$C_2$haloalkoxy; fluorine, chlorine, bromine, iodine; nitro; cyano; phenyl which is unsubstituted or substituted up to three times (where the phenyl substituents are selected from $C_1$–$C_4$alkyl, $C_1$–$C_4$alkoxy, $C_1$–$C_4$haloalkyl, $C_1$–$C_4$haloalkoxy, hydroxyl, halogen, nitro, and cyano); $C_1$–$C_4$hydroxyalkyl, which can be O-alkylated($C_1$–$C_4$); $C_1$–$C_4$alkoxycarbonyl, N-methyl-N-methoxycarbamoyl and unsubstituted or substituted $C_2$–$C_5$alkenyl, whose possible substituents are selected from halogen and $C_1$–$C_2$alkoxy.

11) Another important group among the compounds of subgroup 9) are those in which $R_3$ is a substituted ethynylphenyl group, the substituent on the ethynyl group being a five- or six-membered heteroaryl ring which is unsubstituted or substituted up to three times by halogen (e.g. Cl or Br), cyano, $C_1$–$C_4$alkyl (e.g. methyl, ethyl, isopropyl), $C_1$–$C_4$alkoxy (e.g. methoxy) or hydroxyl.

12) Among the last-mentioned heteroarylethynylphenyl compounds of subgroup 11), those are preferred in which the heteroaryl ring is selected from pyridine, pyrimidine, pyrazine, pyridazine, triazine, (iso)thiazole, (is)oxazole, pyrrole, pyrazole, imidazole, triazole and thiophene, and which is unsubstituted or substituted by up to three substituents selected from methyl, ethyl, isopropyl, CN, halogen (especially chlorine), methoxy and hydroxyl.

Derivatives having unsubstituted, mono- and disubstituted heteroaryl radicals are an important group of active ingredients. They include pyrazinylethynylphenyl and pyridinylethynylphenyl derivatives and others.

13) Within the subgroup 10), those compounds are preferred active substances in which the substituent on the ethynyl group is selected from $C_1$–$C_4$alkyl (e.g. methyl, ethyl, isopropyl, n-butyl); $C_1$–$C_4$alkoxy (e.g. methoxy, ethoxy); $C_1$–$C_2$haloalkyl (e.g. $CF_3$); $C_1$–$C_2$haloalkoxy (e.g. $OCF_3$); chlorine, bromine, iodine; nitro; cyano; $C_1$–$C_4$hydroxyalkyl, which can be O—$C_1$–$C_4$alkylated (e.g.

O-methylated); $C_1$–$C_4$alkoxycarbonyl (e.g. methoxycarbonyl); N-methyl-N-methoxycarbamoyl and unsubstituted or substituted $C_2$–$C_5$alkenyl (e.g. allyl, methallyl, butenyl), whose possible substituents are selected from halogen (e.g. chlorine) and methoxy.

Important compounds as active ingredients and intermediates in this last-mentioned group are, for example, those in which the substituent $R_3$ is a hydroxyalkylethynylphenyl group.

14) Compounds of the formula I are furthermore preferred in which the X=C double bond has the E form. This preference also applies to all subgroups individually mentioned above.

15) In the compounds of group 9) and the subgroups derived therefrom, one of the preferred subgroups is that in which the substituent $R_3$ is an unsubstituted or substituted 3- or 4-($C_2$–$C_4$alkynyl)phenyl group, i.e. the substituted or unsubstituted $C_2$–$C_4$alkynyl radical is linked to the molecule via the phenyl ring in the meta- or para-position.

The preferred individual compounds include the compounds Nos. 1.1; 1.6; 1.8; 1.12; 1.13; 1.15; 1.28; 1.55; 1.56; 1.68; 1.77; 1.85; 1.87; 1.88; Nos. 2.1; 2.6; 2.8; 2.12; 2.13; 2.15; 2.28; 2.55; 2.56; 2.68; 2.77; 2.85; 2.87; 2.88; Nos. 3.1; 3.6; 3.8; 3.12; 3.13; 3.15; 3.28; 3.55; 3.56; 3.68; 3.77; 3.85; 3.87; 3.88, mentioned further below, and also the compounds of Tables 4 and 4a listed herein.

A) To prepare a compound of the formula I in which X, Y, $R_1$, $R_2$, $R_3$ and $R_4$ are as defined for formula I, it is possible to proceed as follows.

An oxime of the general formula II

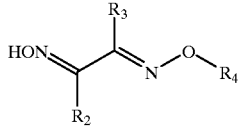

II in which $R_2$–$R_4$ are as defined above, is allowed to react with a benzyl derivative of the general formula III:

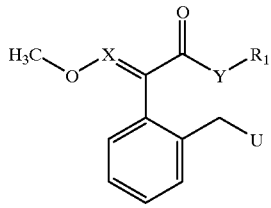

III in which $R_1$, X and Y are as defined above and U is a leaving group.

This reaction is a nucleophilic substitution, which can be carried out under the reaction conditions customary with respect to this. The leaving group U present in the benzyl derivative of the formula III is preferably to be understood as meaning chlorine, bromine, iodine, mesyloxy, benzenesulfonyloxy, nitrobenzenesulfonyloxy or tosyloxy. The reaction is expediently carried out in an inert organic diluent, such as a cyclic ether, e.g. tetrahydrofuran or dioxane, acetone, acetonitrile, dimethylformamide or dimethyl sulfoxide, in the presence of a base, such as sodium hydride, sodium carbonate or potassium carbonate, sodium amide, a tertiary amine, e.g. a trialkylamine, in particular diazabicyclononane or diazabicycloundecane, or silver oxide, at temperatures between −20° C. and +80° C., preferably in the temperature range from 0° C. to 50° C.

As an alternative, the reaction can be carried out at room temperature with phase-transfer catalysis in an organic solvent, for example toluene, in the presence of an aqueous basic solution, e.g. sodium hydroxide solution, and of a phase-transfer catalyst, for example tetrabutylammonium hydrogen sulfate.

B) To obtain a compound of the formula I in which Y is NH ($C_1$–$C_4$alkyl), the underlying compound of the formula I in which Y=$OCH_3$ is reacted, for example, with $C_1$–$C_4$alkylamine, e.g. methylamine. The reaction is expediently carried out in ethanol, which is already used as a solvent for alkylamines, at temperatures between 0° C. and 40° C., preferably at room temperature.

The isolation and purification of the compounds of the formula I prepared in this way can be carried out by methods known per se. Isomer mixtures, e.g. E/Z isomer mixtures, obtained can likewise be separated into the pure isomers by methods known per se, for example by chromatography or fractional crystallization.

The oximes of the general formula II used as starting materials are prepared by reacting a ketone of the general formula IV

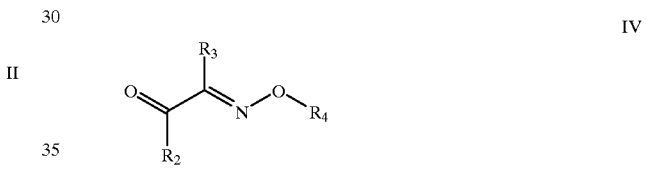

IV with hydroxylamine or one of its salts, e.g. the hydrochloride. The reaction is expediently carried out in pyridine or methanol as a solvent, a base being needed when using methanol, e.g. an alkali metal carbonate such as potassium carbonate, a tertiary amine such as triethylamine or diazabicyclononane, pyridine or silver oxide, at temperatures between −20° C. and +80° C. or the boiling point of methanol, preferably in the temperature range from 0° C. to 50° C.

The ketones of the general formula IV are either known or can be prepared by known methods (e.g. EP 56161; Arthur F. Ferris, J. Org. Chem. 24, 1726 (1959); and J. Irurre Perez et al., An.Quim. 75, 958 (1979)). The still-novel compounds of the formulae II and IV are likewise the subject of the present invention.

The starting materials of the formula III can also be prepared in a manner known per se, e.g. as described in the European Patent Publication EP-A-203 606 and in the literature cited there or in Angew. Chem. 71, 349–365 (1959).

C) To prepare a compound of the formula I in which X, Y, $R_1$, $R_2$ and $R_4$ are as defined for formula I and $R_3$ is substituted or unsubstituted benzyl or substituted or unsubstituted heteroarylmethyl, substituted or unsubstituted biphenyl or substituted or unsubstituted $C_2$–$C_4$alkynylphenyl, an oxime of the general formula V

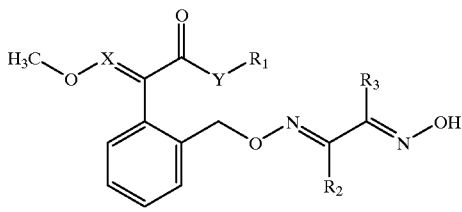

in which X, Y, $R_1$, $R_2$ and $R_3$ are as defined above, is reacted with a compound of the general formula

U—$R_4$     VI in which $R_4$ is defined as under formula I and U is as defined under formula III.

This reaction is a nucleophilic substitution, such as is described under A).

C.a) To prepare an oxime of the formula V, in which X, Y, $R_1$, $R_2$ and $R_3$ are as defined under C), a ketone of the general formula VII

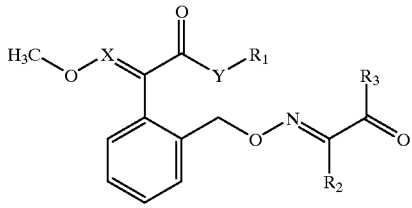

in which X, Y, $R_1$, $R_2$ and $R_3$ are as defined above, can be reacted with hydroxylamine or one of its salts, e.g. the hydrochloride. This reaction expediently takes place in pyridine or methanol as a solvent, a base being needed when using methanol, e.g. an alkali metal carbonate (such as potassium carbonate), a tertiary amine (such as triethylamine or diazabicyclononane, pyridine or silver oxide), at temperatures between −20° C. and +80° C. or the boiling point of methanol, preferably in the temperature range from 0° C. to 50° C.

The preparation of the ketone of the general formula VII is carried out analogously to the method described under A). Similar ketones and their preparation are described, for example, in EP-370 629, EP-506 149, EP-403 618, EP-414 153, EP-463 488, EP-472 300, EP-460 575, WO-92/18494 and elsewhere.

D) A compound of the formula I, in which X, Y, $R_1$ to $R_4$ are as defined for formula I, can be prepared by methylation of an enol or oxime of the general formula VIII

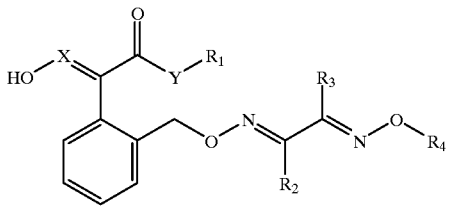

in which X, Y, $R_1$ to $R_4$ are as defined above, with a methylating agent, e.g. methyl iodide, dimethyl sulfate or diazomethane. The reaction is expediently carried out in the presence of a base, e.g. potassium carbonate or sodium hydride, in a suitable solvent and at suitable reaction temperatures (see, for example, H. S. Anker and H. T. Clarke; Organic Synthesis, Coll. Vol. 3, 172).

D.a) A compound of the formula VIII, in which X, Y, $R_1$ to $R_4$ are as defined for formula I, where $R_3$ has a meaning other than "substituted or unsubstituted benzyl" and "substituted or unsubstituted heteroarylmethyl", can also be prepared by nitrosation from a phenylacetic acid derivative of the formula IX

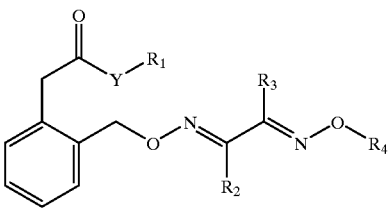

in which Y and $R_1$ to $R_4$ are as defined above, using a formic acid ester (e.g. $HCOOCH_3$) in the presence of a base analogously to the method described in EP-A-178 826 (X=CH), or from IX using nitrous acid HONO or a nitrous acid ester in the presence of a base or acid analogously to the method described in EP-A-254 426. A compound of the formula I can be obtained from a compound VIII, as described under D), by methylation.

D.b) A further possibility of synthesizing a compound of the formula I consists in the following reaction:

a ketoester of the formula X

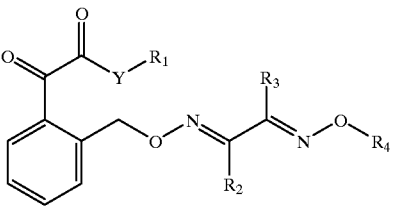

in which Y and $R_1$ to $R_4$ are as defined according to formula I, is reacted with methoxymethylenetriphenylphosphorane analogously to the method described in EP-A-178 826 or with O-methylhydroxylamine (or a salt thereof) analogously to the method described in EP-A-254 426.

The novel compounds of the formulae VII, VIII, IX and X are also a subject of the invention.

It has now been found that compounds of the formula I have, for practical needs, a particularly favourable microbicial spectrum for the control of phytopathogenic microorganisms, in particular fungi. They have very advantageous curative, preventive and in particular systemic properties and can be employed for the protection of numerous plants. Using the active ingredients of the formula I, the pests occurring can be controlled or destroyed on plants or parts of plants (fruits, flowers, foliage, stems, bulbs, roots) of different crops of useful plants, even parts of plants growing later being spared from phytopathogenic microorganisms.

The compounds of the formula I can furthermore be employed as dressing agents for the treatment of seed (fruits, bulbs, grains) and plant seedlings, i.e. for treating propagation material of any species, for protection from fungal infections and against phytopathogenic fungi occurring in the soil.

Compounds of the formula I are active, for example, against the following classes of related phytopathogenic fungi: Fungi imperfecti (in particular Botrytis, Pyricularia, Helminthosporium, Fusarium, Septoria, Cercospora, Cercosporella and Alternaria); Basidiomycetes (e.g. Rhizoctonia, Hemileia, Puccinia); Ascomycetes (e.g. Venturia and Erysiphe, Podosphaera, Monilinia, Uncinula), but also especially against Oomycetes (e.g. Phytophthora, Peronospora, Bremia, Pythium, Plasmopara). Compounds of the formula I also have insecticidal and acaricidal action against sucking and feeding insects and insect stages and also against pests of the order Acarina.

The following plant species, for example, count in the context of this invention as target crops for the phytoprotective use disclosed herein: cereals (wheat, barley, rye, oats, triticale, rice, maize, sorghum and related species); beets (sugar and fodder beets); pomes, drupes and berries (apples, pears, plums, peaches, almonds, cherries, strawberries, gooseberries, raspberries and blackberries); legumes (beans, lentils, peas, soya); oil crops (rape, mustard, poppy, olives, sunflowers, coconut, castor, cocoa, peanuts); cucurbits (pumpkins, cucumbers, melons); fibre plants (cotton, flax, hemp, jute); citrus fruits (oranges, lemons, pomelos, mandarins), vegetable varieties (spinach, head lettuce, asparagus, cabbage species, carrots, onions, tomatoes, potatoes, paprika); Lauraceae (avocado, cinnamomum, camphor) or plants such as tobacco, nuts, coffee, sugar cane, tea, pepper and other spice plants, grapevines, hops, aubergines, bananas and natural rubber plants as well as flowers and decorative plants.

Active ingredients of the formula I are customarily used in the form of combinations and can be added simultaneously or successively with further active ingredients to the surface or plants to be treated. These further active ingredients can be fertilizers, trace element providers or other preparations affecting plant growth. Selective herbicides as well as insecticides, fungicides, bactericides, nematicides, molluscicides or mixtures of several of these preparations can be used here together, if desired, with further carriers, surfactants or other application-promoting additives customary in formulation technology without the efficacy of the compounds of the formula I being adversely affected.

Suitable carriers and additives can be solid or liquid and correspond to the substances suitable in formulation technology, e.g. natural or regenerated mineral substances, solvents, dispersants, wetting agents, adherents, thickeners, binders or fertilizers.

Possible solvents are: aromatic hydrocarbons, preferably the fractions $C_8$ to $C_{12}$, e.g. xylene mixtures or substituted naphthalenes, phthalic acid esters such as dibutyl or dioctyl phthalate, aliphatic hydrocarbons such as cyclohexane or paraffins, alcohols and glycols as well as their ethers and esters, such as ethanol, ethylene glycol, ethylene glycol monomethyl ether or ethyl ether, ketones such as cyclohexanone, strongly polar solvents, such as N-methyl-2-pyrrolidone, dimethyl sulfoxide or dimethylformamide, as well as, if desired, epoxidized vegetable oils such as epoxidized coconut oil or soya oil; or water.

Solid carriers used, e.g. for dusting compositions and dispersible powders, are generally ground natural minerals, such as calcite, talc, kaolin, montmorillonite or attapulgite.

Particularly advantageous application-promoting additives which can lead to a great reduction in the application rate are furthermore natural (animal or vegetable) or synthetic phospholipids from the cephalins and lecithins series which can be obtained, for example, from soya beans.

Suitable surface-active compounds are, depending on the nature of the active ingredient of the formula I to be formulated, non-ionic, cationic and/or anionic surfactants having good emulsifying, dispersing and wetting properties. Surfactants are also understood as meaning surfactant mixtures.

Suitable anionic surfactants are both so-called water-soluble soaps, and water-soluble synthetic surface-active compounds.

Soaps which may be mentioned are the alkali metal, alkaline earth metal or, if desired, substituted ammonium salts of higher fatty acids ($C_{10}$–$C_{22}$), e.g. the sodium or potassium salts of oleic or stearic acid, or of natural fatty acid mixtures which can be obtained, for example, from coconut or tallow oil. The fatty acid methyltauride salts may also be mentioned.

Possible non-ionic surfactants are polyglycol ether derivatives of aliphatic or cycloaliphatic alcohols, saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols.

Examples of non-ionic surfactants which may be mentioned are nonylphenol polyethoxyethanols, castor oil polyglycol ethers, polypropylene-polyethylene oxide adducts, tributylphenoxypolyethoxyethanol, polyethylene glycol and octylphenoxypolyethoxyethanol.

Fatty acid esters of polyoxyethylenesorbitan such as polyethoxyethylenesorbitan trioleate are furthermore also suitable.

The cationic surfactants are especially quaternary ammonium salts, which as N substituents contain at least one alkyl radical having 8 to 22 C atoms and, as further substituents, contain lower, free or halogenated alkyl, benzyl or hydroxyalkyl radicals.

The anionic, non-ionic or cationic surfactants customary in formulation technology are known to the person skilled in the art or can be inferred from the relevant technical literature:
"Mc Cutcheon's Detergents and Emulsifiers Annual", Mc Publishing Corp., Glen Rock, N.J., 1988.
M. and J. Ash, "Encyclopedia of Surfactants", Vol. I–III, Chemical Publishing Co., New York, 1980–1981.
Dr. Helmut Stache "Tensid-Taschenbuch" [Surfactant Handbook], Carl Hanser Verlag, Munich/Vienna 1981.

The agrochemical preparations generally contain 0.1 to 99%, in particular 0.1 to 95%, of active ingredient of the formula I, 99.9 to 1%, in particular 99.9 to 5%, of a solid or liquid additive and 0 to 25%, in particular 0.1 to 25%, of a surfactant.

While more concentrated compositions are preferred as commercially available goods, the end user generally uses diluted compositions.

The compositions can also contain further additives such as stabilizers, antifoams, viscosity regulators, binders, adherents and fertilizers or other active ingredients to achieve specialized effects.

The formulations, i.e. the compositions, preparations or combinations comprising the active ingredient of the formula I and, if desired, a solid or liquid additive are prepared in a known manner, e.g. by intimately mixing and/or grinding the active ingredient with an extender, e.g. with a solvent (mixture), a solid carrier, and, if desired, surface-active compounds (surfactants).

A preferred method of applying an active ingredient of the formula I or an agrochemical composition which contains at least one of these active ingredients is application to the foliage (foliar application). Application frequency and application rate in this case depend on the infestation pressure of the causative organism concerned. The active ingredients of the formula I, however, can also reach the plant via the soil through the root network (systemic action) by saturating the site of the plant with a liquid preparation or incorporating the substances into the soil in solid form, e.g. in the form of granules (soil application). In paddy rice crops, such granules can be added to the flooded paddy field. The compounds of the formula I, however, can also be applied to seed grains (coating) by either saturating the grains in a liquid preparation of the active ingredient or coating them with a solid preparation. Fundamentally, any type of propagation material of a plant can be protected using compounds of the formula I, e.g. the seed, roots, stalk, twigs or shoots.

The compounds of the formula I are employed here in unmodified form or preferably together with the auxiliaries customary in formulation technology. For this purpose, they are expediently processed in a known manner, for example, to give emulsion concentrates, spreadable pastes, directly sprayable or dilutable solutions, diluted emulsions, wettable powders, soluble powders, dusting compositions or granules (by encapsulation in, for example, polymeric substances). The application methods such as spraying, atomizing, dusting, broadcasting, spreading or watering, and also the nature of the compositions, are chosen according to the desired aims and the given ratios. Favourable application rates are in general 1 g to 2 kg of active substance (AS) per ha, preferably 25 g to 800 g of AS/ha and particularly preferably 50 g to 400 g of AS/ha. When used as seed dressing agents, doses of 0.001 g to 1.0 g of active ingredient per kg of seed are advantgeously used.

The following examples serve to illustrate the invention in greater detail, without restricting the latter.

1. PREPARATION EXAMPLES

Example H-1

Preparation of the compound

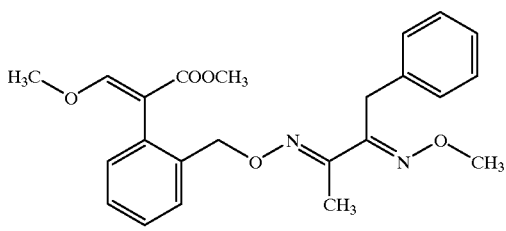

0.22 g of a 60% sodium hydride dispersion is washed with hexane and treated with 5 ml of N,N-dimethylformamide. 1.43 g of methyl 2-(α-bromo-o-tolyl)-3-methoxyacrylate and 1.03 g of 3-methoximino-4-phenyl-2-butanone oxime are added to this suspension and the reaction mixture is stirred for one hour. It is then treated with ice-water, the oil formed crystallizing after a short time. The crystals are filtered off with suction, washed with water and recrystallized from ethyl acetate/hexane. The final product is obtained in the form of white crystals of m.p. 124–126° C. (Compound No. 1.1).

Example H-2

Preparation of the compound

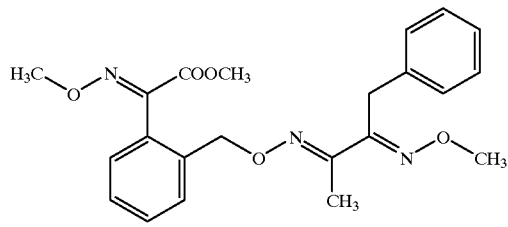

0.36 g of a 60% sodium hydride dispersion is washed with hexane and treated with 10 ml of N,N-dimethylformamide. 2.55 g of methyl 2-(2-bromomethylphenyl)glyoxylate O-methyloxime and 1.83 g of 3-methoxyimino-4-phenyl-2-butanone oxime are added to the suspension and the reaction mixture is stirred for one hour. It is then treated with ice-water, the oil formed crystallizing after a short time. The crystals are filtered off with suction, washed with water and recrystallized from diethyl ether/hexane. The final product is obtained in the form of yellowish crystals of m.p. 86–88° C. (Compound No. 2.1).

Example H-3

Preparation of the compound

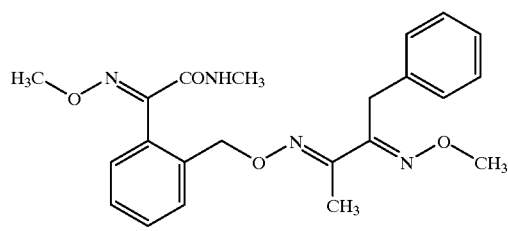

1.0 g of the compound obtained in H-2 is stirred at room temperature for 2 hours in 5 ml of a 33% ethanolic methylamine solution. Ethanol and excess methylamine are distilled off and the residue is crystallized from diethyl ether/hexane. The final product is obtained in the form of yellowish crystals of m.p. 119–120° C. (Compound No. 3.1).

The following compounds, which belong to the restricted range of the present invention, can be prepared in this manner or analogously to one of the methods indicated above.

[$^1$H-NMR: Chemical shifts data in δ(ppm) in CDCl$_3$.]

Example H-4

Preparation of the compound

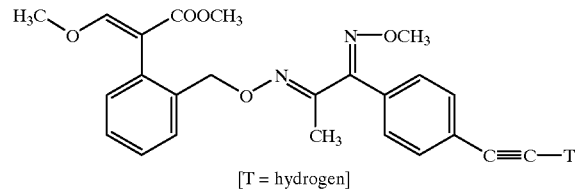

[T = hydrogen]

9.9 g of K$_2$CO$_3$ are added to a solution of 6.2 g of 2-hydroximino-3-(4-ethynylphenyl)-3- methoximinopropane and 8.2 g of methyl 2-(α-bromo-o-tolyl)-3-methoxyacrylate in 200 ml of acetonitrile. The reaction mixture is stirred at 65° C. for 6 hours and then filtered, and the filtrate is evaporated. The oily residue is chromatographed on silica gel (hexane/diisopropyl ether/toluene 2:1:1). 9.2 g of the title compound (No. 1.88) are obtained; m.p. 127–129° C.

Example H-5

Preparation of the compound according to Example H-4, in which T=3-pyridyl.

0.3 g of copper(I) iodide and 0.8 g of Pd(TPP)$_2$Cl$_2$ are added to a solution of 20 g of the compound obtained according to Example H-4 and 10 g of 3-iodopyridine in 400 ml of triethylamine and 50 ml of tetrahydrofuran. The reaction mixture is stirred at 65° C. for 2 hours and then filtered, and the filtrate is evaporated. The residual oil is chromatographed on silica gel (ethyl acetate/hexane 1:2). 19.7 g of the title compound (No. 4.14) are obtained; m.p. 106–108° C. [TPP=triphenylphosphine].

Example H-6

Corresponding to Example H-4, the compound No. 2.88 mentioned in Table 2 is obtained from 2-hydroximino-3-(4-ethynylphenyl)-3-methoximinopropane and methyl 2-(α-bromo-o-tolyl)glyoxylate O-methyloxime after chromatographic purification.

Example H-7

The corresponding glyoxylic acid methylamide O-methyloxime mentioned as No. 3.88 in Table 3 can be obtained from the methyl glyoxylate O-methyloxime obtained according to Example H-6 by reaction with ethanolic methylamine solution.

TABLE 1

| Ex. No. | R$_2$ | R$_3$ | R$_4$ | M.p. or $^1$H—NMR of R$_2$ |
|---|---|---|---|---|
| 1.1 | CH$_3$ | CH$_2$—C$_6$H$_5$ | CH$_3$ | 124–126° C. |
| 1.2 | CH$_3$ | CH$_2$—C$_6$H$_4$—OCH$_3$ (4-) | CH$_3$ | 84–86° C. |
| 1.3 | CH$_3$ | CH$_2$—C$_6$H$_4$—Cl (3-) | CH$_3$ | |
| 1.4 | CH$_3$ | CH$_2$—C$_6$H$_4$—Cl (2-) | CH$_3$ | |
| 1.5 | CH$_3$ | CH$_2$—C$_6$H$_4$—CF$_3$ (4-) | CH$_3$ | |
| 1.6 | CH$_3$ | CH$_2$—C$_6$H$_4$—CF$_3$ (3-) | CH$_3$ | |
| 1.7 | CH$_3$ | CH$_2$—C$_6$H$_4$—F (4-) | CH$_3$ | |

TABLE 1-continued
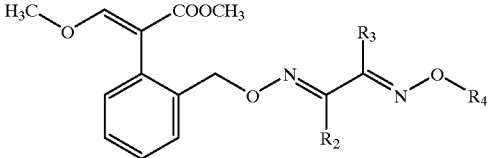
| Ex. No. | R$_2$ | R$_3$ | R$_4$ | M.p. or $^1$H—NMR of R$_2$ |
|---|---|---|---|---|
| 1.8 | CH$_3$ | 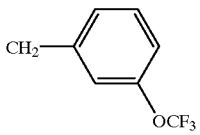 | CH$_3$ | |
| 1.9 | CH$_3$ | 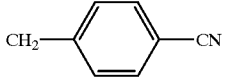 | CH$_3$ | |
| 1.10 | CH$_3$ |  | CH$_3$ | |
| 1.11 | CH$_3$ | 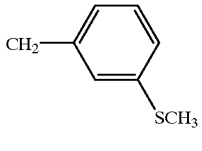 | CH$_3$ | |
| 1.12 | CH$_3$ | 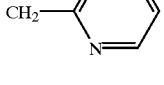 | CH$_3$ | |
| 1.13 | CH$_3$ | 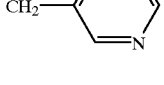 | CH$_3$ | |
| 1.14 | CH$_3$ | 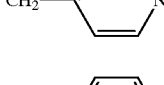 | CH$_3$ | |
| 1.15 | H | 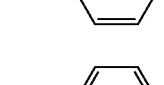 | CH$_3$ | |
| 1.16 |  |  | CH$_3$ | |
| 1.17 | CH$_3$CH$_2$ | 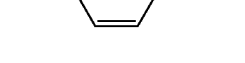 | CH$_3$ | |
| 1.18 | CH$_3$ | 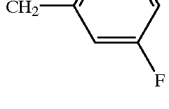 | CH$_3$CH$_2$ | |

TABLE 1-continued

[Structure: methyl (E)-2-methoxyimino-2-[2-({[(1E,2E)-2-(alkoxyimino)-1-R2-2-R3-ethylidene]aminooxy}methyl)phenyl]acetate scaffold with R2, R3, R4 substituents]

| Ex. No. | R2 | R3 | R4 | M.p. or ¹H—NMR of R2 |
|---|---|---|---|---|
| 1.19 | $CH_3$ | $CH_2$–phenyl | t-Butyl | |
| 1.20 | $CH_3$ | $CH_2$–phenyl | $HC\equiv C-CH_2$ | |
| 1.21 | $CH_3$ | $CH_2$–phenyl | cyclopropyl–$CH_2$ | |
| 1.22 | $CH_3$ | $CH_2$–phenyl | $H_2C=C(Cl)CH_2$ | |
| 1.23 | $CH_3$ | $CH_2$–phenyl | $F_3CCH_2$ | |
| 1.24 | $CH_3$ | $CH_2$–phenyl | $FCH_2CH_2$ | |
| 1.25 | $CH_3$ | $CH_2$–phenyl | $F_3CCH_2CH_2CH_2$ | |
| 1.26 | $CH_3$ | $CH_2$–phenyl | 2,2-dichlorocyclopropyl–$CH_2$ | |
| 1.27 | $CH_3$ | $CH_2$–(2-naphthyl) | $CH_3$ | |
| 1.28 | $CH_3$ | O–phenyl | $CH_3$ | 144–145° C. |
| 1.29 | $CH_3$ | O–(4-chlorophenyl) | $CH_3$ | |

TABLE 1-continued

[Structure: methyl (E)-2-[2-[[(oximino)methyl]phenyl]-3-methoxyacrylate with R2, R3, R4 substituents on the bis-oxime ether]

| Ex. No. | R2 | R3 | R4 | M.p. or ¹H—NMR of R2 |
|---------|-----|-----|-----|----------------------|
| 1.30 | $CH_3$ | 3-chlorophenoxy | $CH_3$ | |
| 1.31 | $CH_3$ | 2-chlorophenoxy | $CH_3$ | |
| 1.32 | $CH_3$ | 4-(trifluoromethyl)phenoxy | $CH_3$ | |
| 1.33 | $CH_3$ | 3-(trifluoromethyl)phenoxy | $CH_3$ | |
| 1.34 | $CH_3$ | 4-(methylthio)phenoxy | $CH_3$ | |
| 1.35 | $CH_3$ | 4-(methylsulfinyl)phenoxy | $CH_3$ | |
| 1.36 | $CH_3$ | 4-(methylsulfonyl)phenoxy | $CH_3$ | |
| 1.37 | $CH_3$ | 4-(butylthio)phenoxy | $CH_3$ | |
| 1.38 | $CH_3$ | 4-(butylsulfinyl)phenoxy | $CH_3$ | |
| 1.39 | $CH_3$ | 4-(butylsulfonyl)phenoxy | $CH_3$ | |

TABLE 1-continued
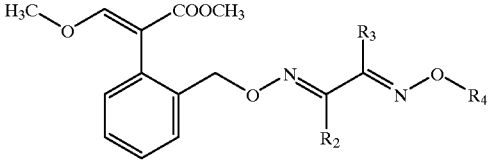
| Ex. No. | R₂ | R₃ | R₄ | M.p. or ¹H—NMR of R₂ |
|---|---|---|---|---|
| 1.40 | CH₃ | 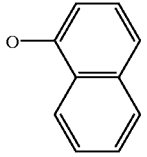 | CH₃ | |
| 1.41 | CH₃ | 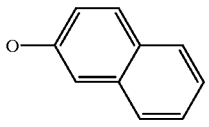 | CH₃ | |
| 1.42 | CH₃ | 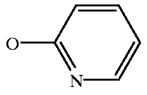 | CH₃ | |
| 1.43 | CH₃ | 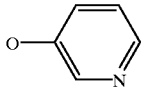 | CH₃ | |
| 1.44 | CH₃ | 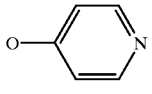 | CH₃ | |
| 1.45 | CH₃ | 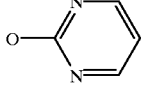 | CH₃ | |
| 1.46 | CH₃ | 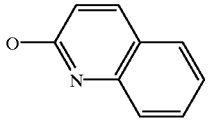 | CH₃ | |
| 1.47 | CH₃ | 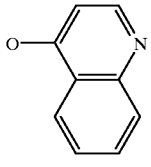 | CH₃ | |
| 1.48 | CH₃ | 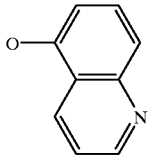 | CH₃ | |

TABLE 1-continued
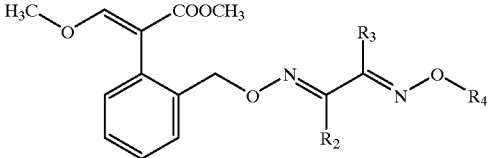
| Ex. No. | R₂ | R₃ | R₄ | M.p. or ¹H—NMR of R₂ |
|---|---|---|---|---|
| 1.49 | CH₃ | 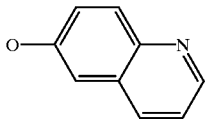 | CH₃ | |
| 1.50 | CH₃ | 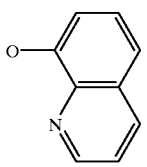 | CH₃ | |
| 1.51 | CH₃ | 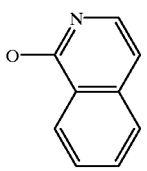 | CH₃ | |
| 1.52 | CH₃ | 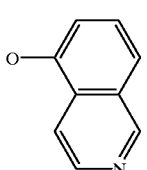 | CH₃ | |
| 1.53 | CH₃ | 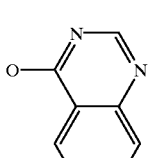 | CH₃ | |
| 1.54 | CH₃ | 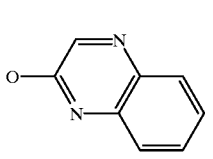 | CH₃ | |
| 1.55 | CH₃ | 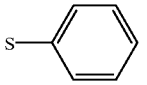 | CH₃ | 94–95° C. |
| 1.56 | CH₃ | 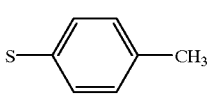 | CH₃ | 1.66 |
| 1.57 | H | 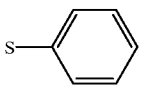 | CH₃ | |

TABLE 1-continued
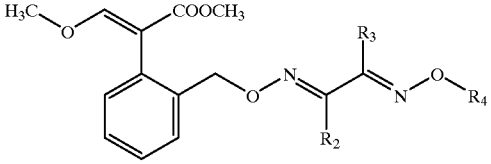
| Ex. No. | R₂ | R₃ | R₄ | M.p. or ¹H—NMR of R₂ |
|---|---|---|---|---|
| 1.58 |  | 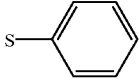 | CH₃ | |
| 1.59 | CH₃CH₂CH₂ | 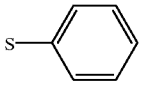 | CH₃ | |
| 1.60 | CH₃(CH₂)₃ | 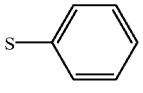 | CH₃ | |
| 1.61 | (CH₃)₂CH | 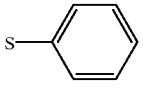 | CH₃ | |
| 1.62 | CH₃ |  | CH₃ | |
| 1.63 | CH₃ |  | CH₃ | |
| 1.64 | CH₃ | 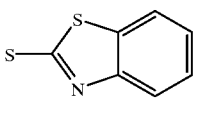 | CH₃ | |
| 1.65 | CH₃ | 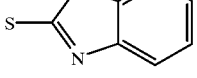 | CH₃ | |
| 1.66 | CH₃ | 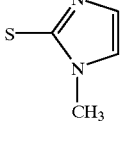 | CH₃ | |
| 1.67 | CH₃ | 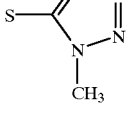 | CH₃ | |
| 1.68 | CH₃ | SCH₃ | CH₃ | 2.09 |
| 1.69 | CH₃ | SCH₂CH₃ | CH₃ | |
| 1.70 | CH₃ | SCH₂CH₂CH₃ | CH₃ | |
| 1.71 | CH₃ | S(CH₂)₅CH₃ | CH₃ | |
| 1.72 | CH₃ | SCH₃ | CH₃CH₂ | |

TABLE 1-continued

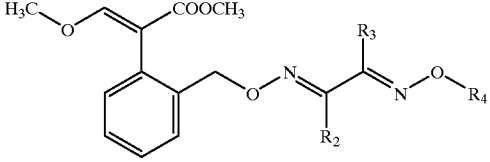

| Ex. No. | R$_2$ | R$_3$ | R$_4$ | M.p. or $^1$H—NMR of R$_2$ |
|---|---|---|---|---|
| 1.73 | CH$_3$ | SCH$_3$ | 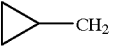 | |
| 1.74 | CH$_3$ | SCH$_3$ | F$_3$CCH$_2$ | |
| 1.75 | CH$_3$ | SCH$_3$ | FCH$_2$CH$_2$ | |
| 1.76 | CH$_3$ | SCH$_3$ | F$_3$C$_{CH2}$CH$_2$CH$_2$ | |
| 1.77 | CH$_3$ | OCH$_3$ | CH$_3$ | |
| 1.78 | CH$_3$ | OCH$_2$CH$_3$ | CH$_3$ | |
| 1.79 | CH$_3$ | OCH$_2$CF$_3$ | CH$_3$ | |
| 1.80 | CH$_3$ | OCH$_2$CH$_2$CH$_3$ | CH$_3$ | |
| 1.81 | CH$_3$ | OCH$_2$CH$_2$Cl | CH$_3$ | |
| 1.82 | CH$_3$ | OCH$_2$CH$_2$CH(CH$_3$)$_2$ | CH$_3$ | |
| 1.83 | CH$_3$ | OCH$_2$C(CH$_3$)$_3$ | CH$_3$ | |
| 1.84 | CH$_3$ | O(CH$_2$)$_5$CH$_3$ | CH$_3$ | |
| 1.85 | CH$_3$ | 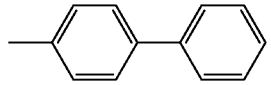 | CH$_3$ | {Isomer A: 2.17 {Isomer B: resin |
| 1.86 | CH$_3$ | 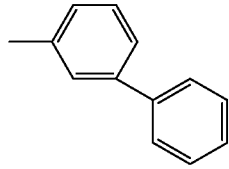 | CH$_3$ | |
| 1.87 | CH$_3$ | 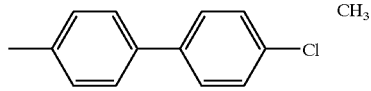 | CH$_3$ | |
| 1.88 | CH$_3$ | 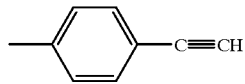 | CH$_3$ | 127–129° C. |

TABLE 2

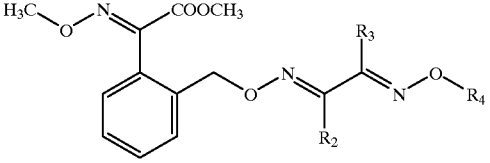

| Ex. No. | R$_2$ | R$_3$ | R$_4$ | M.p. or $^1$H-NMR of R$_2$ |
|---|---|---|---|---|
| 2.1 | CH$_3$ | 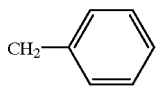 | CH$_3$ | 86–88° C. |

TABLE 2-continued
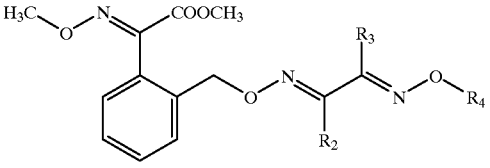
| Ex. No. | R$_2$ | R$_3$ | R$_4$ | M.p. or $^1$H-NMR of R$_2$ |
|---|---|---|---|---|
| 2.2 | CH$_3$ | 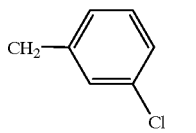 | CH$_3$ | Oil |
| 2.3 | CH$_3$ | 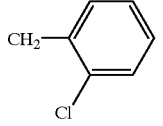 | CH$_3$ | |
| 2.4 | CH$_3$ |  | CH$_3$ | |
| 2.5 | CH$_3$ | 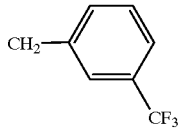 | CH$_3$ | |
| 2.6 | CH$_3$ | 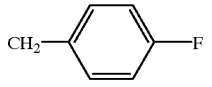 | CH$_3$ | |
| 2.7 | CH$_3$ | 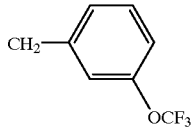 | CH$_3$ | |
| 2.8 | CH$_3$ |  | CH$_3$ | |
| 2.9 | CH$_3$ |  | CH$_3$ | |
| 2.10 | CH$_3$ | 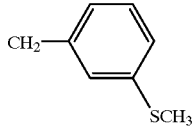 | CH$_3$ | |
| 2.11 | CH$_3$ | (CH$_2$-C$_6$H$_4$-SCH$_3$) | CH$_3$ | |

TABLE 2-continued
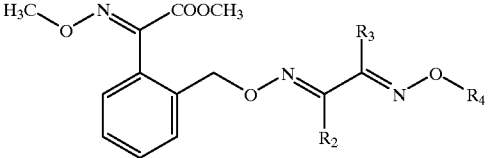
| Ex. No. | R₂ | R₃ | R₄ | M.p. or ¹H-NMR of R₂ |
|---|---|---|---|---|
| 2.12 | CH₃ | 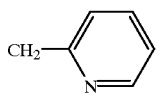 | CH₃ | |
| 2.13 | CH₃ | 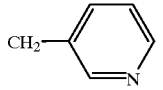 | CH₃ | |
| 2.14 | CH₃ | 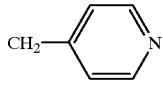 | CH₃ | |
| 2.15 | H | 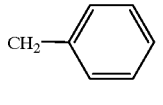 | CH₃ | |
| 2.16 | 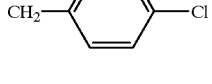 | 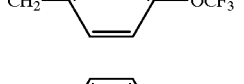 | CH₃ | |
| 2.17 | CH₃CH₂ | 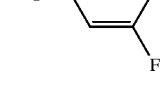 | CH₃ | |
| 2.18 | CH₃ | 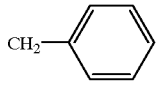 | CH₃CH₂ | |
| 2.19 | CH₃ | 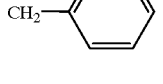 | t-Butyl | |
| 2.20 | CH₃ | 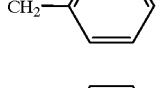 | HC≡C—CH₂ | |
| 2.21 | CH₃ | 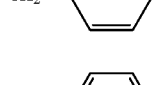 | 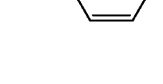—CH₂ | |
| 2.22 | CH₃ | | H₂C=C(Cl)CH₂ | |
| 2.23 | CH₃ | | F₃CCH₂ | |

TABLE 2-continued

Structure: methyl 2-[[[[1-R2-2-R3-2-(R4-oxyimino)ethylidene]amino]oxy]methyl]phenyl (methoxyimino)acetate

| Ex. No. | R₂ | R₃ | R₄ | M.p. or ¹H-NMR of R₂ |
|---|---|---|---|---|
| 2.24 | CH₃ | CH₂–C₆H₅ | FCH₂CH₂ | |
| 2.25 | CH₃ | CH₂–C₆H₅ | F₃CCH₂CH₂CH₂ | |
| 2.26 | CH₃ | CH₂–C₆H₅ | –CH₂–C(Cl)(Cl)-cyclopropyl | |
| 2.27 | CH₃ | CH₂–(2-naphthyl) | CH₃ | |
| 2.28 | CH₃ | O–C₆H₅ | CH₃ | 114° C. |
| 2.29 | CH₃ | O–C₆H₄–4-Cl | CH₃ | |
| 2.30 | CH₃ | O–C₆H₄–3-Cl | CH₃ | |
| 2.31 | CH₃ | O–C₆H₄–2-Cl | CH₃ | |
| 2.32 | CH₃ | O–C₆H₄–4-CF₃ | CH₃ | |
| 2.33 | CH₃ | O–C₆H₄–3-CF₃ | CH₃ | |

TABLE 2-continued
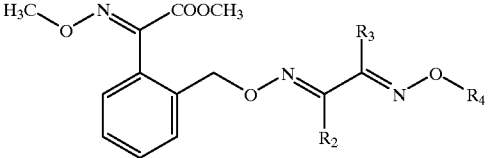
| Ex. No. | R$_2$ | R$_3$ | R$_4$ | M.p. or $^1$H-NMR of R$_2$ |
|---|---|---|---|---|
| 2.34 | CH$_3$ | 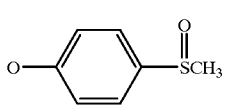 | CH$_3$ | |
| 2.35 | CH$_3$ | 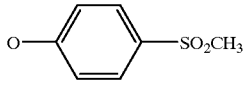 | CH$_3$ | |
| 2.36 | CH$_3$ | 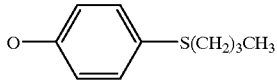 | CH$_3$ | |
| 2.37 | CH$_3$ | 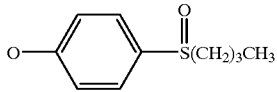 | CH$_3$ | |
| 2.38 | CH$_3$ | 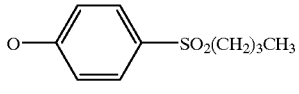 | CH$_3$ | |
| 2.39 | CH$_3$ | 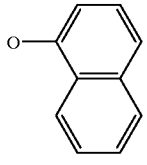 | CH$_3$ | |
| 2.40 | CH$_3$ | 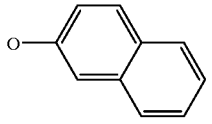 | CH$_3$ | |
| 2.41 | CH$_3$ | 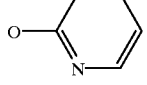 | CH$_3$ | |
| 2.42 | CH$_3$ | 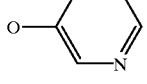 | CH$_3$ | |
| 2.43 | CH$_3$ | 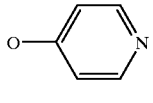 | CH$_3$ | |
| 2.44 | CH$_3$ |  | CH$_3$ | |

TABLE 2-continued
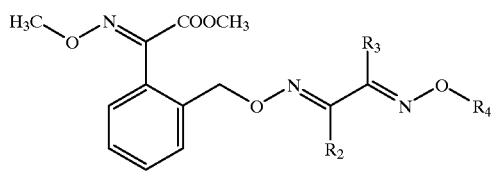
| Ex. No. | R$_2$ | R$_3$ | R$_4$ | M.p. or $^1$H-NMR of R$_2$ |
|---|---|---|---|---|
| 2.45 | CH$_3$ |  | CH$_3$ | |
| 2.46 | CH$_3$ |  | CH$_3$ | |
| 2.47 | CH$_3$ |  | CH$_3$ | |
| 2.48 | CH$_3$ |  | CH$_3$ | |
| 2.49 | CH$_3$ |  | CH$_3$ | |
| 2.50 | CH$_3$ |  | CH$_3$ | |
| 2.51 | CH$_3$ |  | CH$_3$ | |
| 2.52 | CH$_3$ |  | CH$_3$ | |

TABLE 2-continued
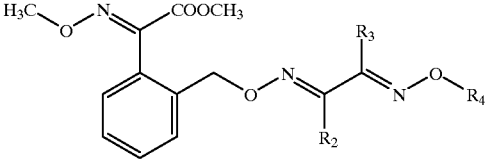
| Ex. No. | R$_2$ | R$_3$ | R$_4$ | M.p. or $^1$H-NMR of R$_2$ |
|---|---|---|---|---|
| 2.53 | CH$_3$ | 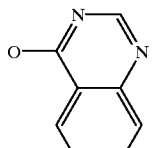 | CH$_3$ | |
| 2.54 | CH$_3$ | 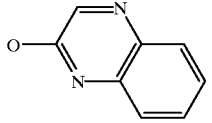 | CH$_3$ | |
| 2.55 | CH$_3$ | 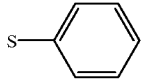 | CH$_3$ | 82° C. |
| 2.56 | CH$_3$ | 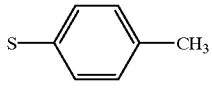 | CH$_3$ | 100–101° C. |
| 2.57 | H | 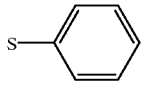 | CH$_3$ | |
| 2.58 | 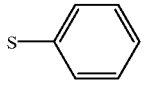 | 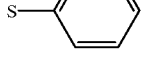 | CH$_3$ | |
| 2.59 | CH$_3$CH$_2$CH$_2$ | 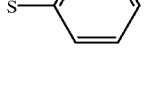 | CH$_3$ | |
| 2.60 | CH$_3$(CH$_2$)$_3$ | 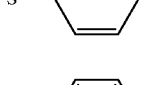 | CH$_3$ | |
| 2.61 | (CH$_3$)$_2$CH | 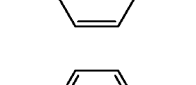 | CH$_3$ | |
| 2.62 | CH$_3$ | 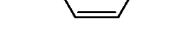 | CH$_3$ | |
| 2.63 | CH$_3$ |  | CH$_3$ | |

TABLE 2-continued

[Structure: methyl (E)-2-[2-((aminooxy)methyl)phenyl]-2-(methoxyimino)acetate derivative with =N-O-R4 and R2, R3 substituents on the oxime carbon]

| Ex. No. | R₂ | R₃ | R₄ | M.p. or ¹H-NMR of R₂ |
|---|---|---|---|---|
| 2.64 | CH₃ | 2-benzothiazolylthio | CH₃ | |
| 2.65 | CH₃ | 2-benzoxazolylthio | CH₃ | |
| 2.66 | CH₃ | (1-methylimidazol-2-yl)thio | CH₃ | |
| 2.67 | CH₃ | (1-methyltetrazol-5-yl)thio | CH₃ | |
| 2.68 | CH₃ | SCH₃ | CH₃ | 71–72° C. |
| 2.69 | CH₃ | SCH₂CH₃ | CH₃ | |
| 2.70 | CH₃ | SCH₂CH₂CH₃ | CH₃ | |
| 2.71 | CH₃ | S(CH₂)₅CH₃ | CH₃ | |
| 2.72 | CH₃ | SCH₃ | CH₃CH₂ | |
| 2.73 | CH₃ | SCH₃ | cyclopropyl-CH₂ | |
| 2.74 | CH₃ | SCH₃ | F₃CCH₂ | |
| 2.75 | CH₃ | SCH₃ | FCH₂CH₂ | |
| 2.76 | CH₃ | SCH₃ | F₃CCH₂CH₂CH₂ | |
| 2.77 | CH₃ | OCH₃ | CH₃ | |
| 2.78 | CH₃ | OCH₂CH₃ | CH₃ | |
| 2.79 | CH₃ | OCH₂CF₃ | CH₃ | |
| 2.80 | CH₃ | OCH₂CH₂CH₃ | CH₃ | |
| 2.81 | CH₃ | OCH₂CH₂Cl | CH₃ | |
| 2.82 | CH₃ | OCH₂CH₂CH(CH₃)₂ | CH₃ | |
| 2.83 | CH₃ | OCH₂C(CH₃)₃ | CH₃ | |
| 2.84 | CH₃ | O(CH₂)₅SCH₃ | CH₃ | |
| 2.85 | CH₃ | 4-biphenylyl | CH₃ | 2.14 |
| 2.86 | CH₃ | 3-biphenylyl | CH₃ | |

TABLE 2-continued

[Structure: methyl ester of methoxyimino group on benzene ring with CH₂-O-N=C(R₂)-C(R₃)=N-O-R₄]

| Ex. No. | R₂ | R₃ | R₄ | M.p. or ¹H-NMR of R₂ |
|---|---|---|---|---|
| 2.87 | CH₃ | 4'-chloro-biphenyl-4-yl | CH₃ | |
| 2.88 | CH₃ | 4-ethynylphenyl | CH₃ | |

TABLE 3

[Structure: N-methylamide of methoxyimino group on benzene ring with CH₂-O-N=C(R₂)-C(R₃)=N-O-R₄]

| Ex. No. | R₂ | R₃ | R₄ | M.p. or ¹H-NMR of R₂ |
|---|---|---|---|---|
| 3.1 | CH₃ | CH₂-phenyl | CH₃ | 119–120° C. |
| 3.2 | CH₃ | CH₂-(4-methoxyphenyl) | CH₃ | 90° C. |
| 3.3 | CH₃ | CH₂-(3-chlorophenyl) | CH₃ | |
| 3.4 | CH₃ | CH₂-(2-chlorophenyl) | CH₃ | |
| 3.5 | CH₃ | CH₂-(4-trifluoromethylphenyl) | CH₃ | |
| 3.6 | CH₃ | CH₂-(3-trifluoromethylphenyl) | CH₃ | |

TABLE 3-continued

[Structure: H3CO-N=C(CONHCH3)-pyridyl-CH2-O-N=C(R2)-C(R3)=N-O-R4]

| Ex. No. | R₂ | R₃ | R₄ | M.p. or ¹H—NMR of R₂ |
|---|---|---|---|---|
| 3.7 | CH₃ | CH₂-(4-F-C₆H₄) | CH₃ | |
| 3.8 | CH₃ | CH₂-(3-OCF₃-C₆H₄) | CH₃ | |
| 3.9 | CH₃ | CH₂-(4-CN-C₆H₄) | CH₃ | |
| 3.10 | CH₃ | CH₂-(4-NO₂-C₆H₄) | CH₃ | |
| 3.11 | CH₃ | CH₂-(3-SCH₃-C₆H₄) | CH₃ | |
| 3.12 | CH₃ | CH₂-(2-pyridyl) | CH₃ | |
| 3.13 | CH₃ | CH₂-(3-pyridyl) | CH₃ | |
| 3.14 | CH₃ | CH₂-(4-pyridyl) | CH₃ | |
| 3.15 | H | CH₂-C₆H₅ | CH₃ | |
| 3.16 | cyclopropyl | CH₂-(4-Cl-C₆H₄) | CH₃ | |
| 3.17 | CH₃CH₂ | CH₂-(4-OCF₃-C₆H₄) | CH₃ | |

TABLE 3-continued

[Structure: H3C-O-N=C(CONHCH3)-C6H4-CH2-O-N=C(R2)-C(R3)=N-O-R4]

| Ex. No. | R₂ | R₃ | R₄ | M.p. or ¹H—NMR of R₂ |
|---|---|---|---|---|
| 3.18 | CH₃ | CH₂-(3-F-C₆H₄) | CH₃CH₂ | |
| 3.19 | CH₃ | CH₂-C₆H₅ | t-Butyl | |
| 3.20 | CH₃ | CH₂-C₆H₅ | HC≡C—CH₂ | |
| 3.21 | CH₃ | CH₂-C₆H₅ | cyclopropyl-CH₂ | |
| 3.22 | CH₃ | CH₂-C₆H₅ | H₂C=C(Cl)CH₂ | |
| 3.23 | CH₃ | CH₂-C₆H₅ | F₃CCH₂ | |
| 3.24 | CH₃ | CH₂-C₆H₅ | FCH₂CH₂ | |
| 3.25 | CH₃ | CH₂-C₆H₅ | F₃CCH₂CH₂CH₂ | |
| 3.26 | CH₃ | CH₂-C₆H₅ | 2,2-dichlorocyclopropyl-CH₂ | |
| 3.27 | CH₃ | CH₂-(2-naphthyl) | CH₃ | |
| 3.28 | CH₃ | O-C₆H₅ | CH₃ | 137° C. |

TABLE 3-continued

[Structure: H3C-O-N=C(CONHCH3)-C6H4-CH2-O-N=C(R2)-C(R3)=N-O-R4]

| Ex. No. | R$_2$ | R$_3$ | R$_4$ | M.p. or $^1$H—NMR of R$_2$ |
|---|---|---|---|---|
| 3.29 | CH$_3$ | O-C$_6$H$_4$-Cl (4-) | CH$_3$ | |
| 3.30 | CH$_3$ | O-C$_6$H$_4$-Cl (3-) | CH$_3$ | |
| 3.31 | CH$_3$ | O-C$_6$H$_4$-Cl (2-) | CH$_3$ | |
| 3.32 | CH$_3$ | O-C$_6$H$_4$-CF$_3$ (4-) | CH$_3$ | |
| 3.33 | CH$_3$ | O-C$_6$H$_4$-CF$_3$ (3-) | CH$_3$ | |
| 3.34 | CH$_3$ | O-C$_6$H$_4$-SCH$_3$ (4-) | CH$_3$ | |
| 3.35 | CH$_3$ | O-C$_6$H$_4$-S(O)CH$_3$ (4-) | CH$_3$ | |
| 3.36 | CH$_3$ | O-C$_6$H$_4$-SO$_2$CH$_3$ (4-) | CH$_3$ | |
| 3.37 | CH$_3$ | O-C$_6$H$_4$-S(CH$_2$)$_3$CH$_3$ (4-) | CH$_3$ | |
| 3.38 | CH$_3$ | O-C$_6$H$_4$-S(O)(CH$_2$)$_3$CH$_3$ (4-) | CH$_3$ | |
| 3.39 | CH$_3$ | O-C$_6$H$_4$-SO$_2$(CH$_2$)$_3$CH$_3$ (4-) | CH$_3$ | |

TABLE 3-continued
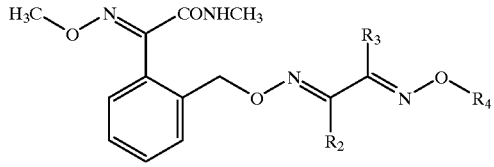
| Ex. No. | R$_2$ | R$_3$ | R$_4$ | M.p. or $^1$H—NMR of R$_2$ |
|---|---|---|---|---|
| 3.40 | CH$_3$ | 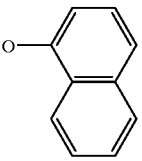 | CH$_3$ | |
| 3.41 | CH$_3$ | 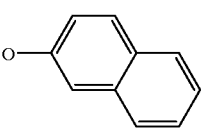 | CH$_3$ | |
| 3.42 | CH$_3$ | 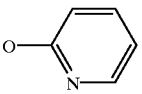 | CH$_3$ | |
| 3.43 | CH$_3$ | 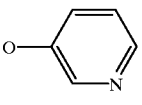 | CH$_3$ | |
| 3.44 | CH$_3$ | 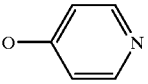 | CH$_3$ | |
| 3.45 | CH$_3$ | 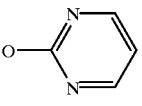 | CH$_3$ | |
| 3.46 | CH$_3$ | 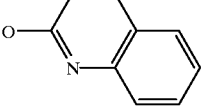 | CH$_3$ | |
| 3.47 | CH$_3$ | 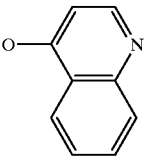 | CH$_3$ | |
| 3.48 | CH$_3$ | 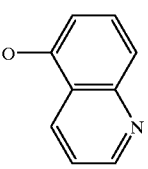 | CH$_3$ | |

TABLE 3-continued

[Structure: H3C-O-N=C(CONHCH3)-C6H4-CH2-O-N=C(R2)-C(R3)=N-O-R4]

| Ex. No. | R₂ | R₃ | R₄ | M.p. or ¹H—NMR of R₂ |
|---|---|---|---|---|
| 3.49 | CH₃ | 6-quinolinyloxy | CH₃ | |
| 3.50 | CH₃ | 8-quinolinyloxy | CH₃ | |
| 3.51 | CH₃ | 1-isoquinolinyloxy | CH₃ | |
| 3.52 | CH₃ | 5-isoquinolinyloxy | CH₃ | |
| 3.53 | CH₃ | 4-quinazolinyloxy | CH₃ | |
| 3.54 | CH₃ | 2-quinoxalinyloxy | CH₃ | |
| 3.55 | CH₃ | phenylthio | CH₃ | 113–115° C. |
| 3.56 | CH₃ | (4-methylphenyl)thio | CH₃ | 109–110° C. |
| 3.57 | H | phenylthio | CH₃ | |

TABLE 3-continued
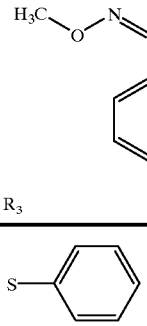
| Ex. No. | R₂ | R₃ | R₄ | M.p. or ¹H—NMR of R₂ |
|---|---|---|---|---|
| 3.58 | 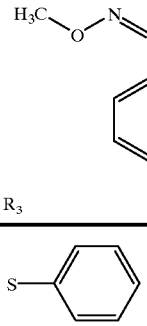 | 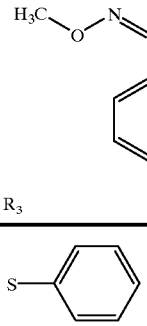 | CH₃ | |
| 3.59 | CH₃CH₂CH₂ | 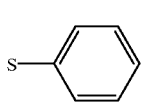 | CH₃ | |
| 3.60 | CH₃(CH₂)₃ | 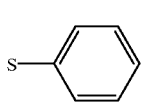 | CH₃ | |
| 3.61 | (CH₃)₂CH | 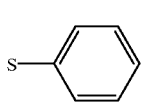 | CH₃ | |
| 3.62 | CH₃ | 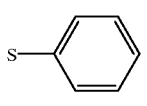 | CH₃ | |
| 3.63 | CH₃ | 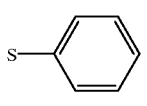 | CH₃ | |
| 3.64 | CH₃ | 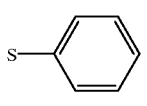 | CH₃ | |
| 3.65 | CH₃ | 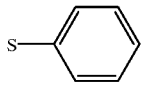 | CH₃ | |
| 3.66 | CH₃ | 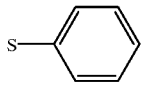 | CH₃ | |
| 3.67 | CH₃ | 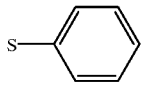 | CH₃ | |
| 3.68 | CH₃ | SCH₃ | CH₃ | 72° C. |
| 3.69 | CH₃ | SCH₂CH₃ | CH₃ | |
| 3.70 | CH₃ | SCH₂CH₂CH₃ | CH₃ | |
| 3.71 | CH₃ | S(CH₂)₅CH₃ | CH₃ | |
| 3.72 | CH₃ | SCH₃ | CH₃CH₂ | |

TABLE 3-continued

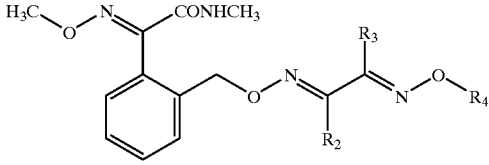

| Ex. No. | R$_2$ | R$_3$ | R$_4$ | M.p. or $^1$H—NMR of R$_2$ |
|---|---|---|---|---|
| 3.73 | CH$_3$ | SCH$_3$ | 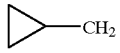 | |
| 3.74 | CH$_3$ | SCH$_3$ | F$_3$CCH$_2$ | |
| 3.75 | CH$_3$ | SCH$_3$ | FCH$_2$CH$_2$ | |
| 3.76 | CH$_3$ | SCH$_3$ | F$_3$CCH$_2$CH$_2$CH$_2$ | |
| 3.77 | CH$_3$ | OCH$_3$ | CH$_3$ | |
| 3.78 | CH$_3$ | OCH$_2$CH$_3$ | CH$_3$ | |
| 3.79 | CH$_3$ | OCH$_2$CF$_3$ | CH$_3$ | |
| 3.80 | CH$_3$ | OCH$_2$CH$_2$CH$_3$ | CH$_3$ | |
| 3.81 | CH$_3$ | OCH$_2$CH$_2$Cl | CH$_3$ | |
| 3.82 | CH$_3$ | OCH$_2$CH$_2$CH(CH$_3$)$_2$ | CH$_3$ | |
| 3.83 | CH$_3$ | OCH$_2$C(CH$_3$)$_3$ | CH$_3$ | |
| 3.84 | CH$_3$ | O(CH$_2$)$_5$CH$_3$ | CH$_3$ | |
| 3.85 | CH$_3$ | 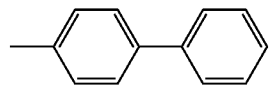 | CH$_3$ | 133–135° C. |
| 3.86 | CH$_3$ | 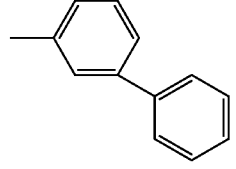 | CH$_3$ | |
| 3.87 | CH$_3$ | 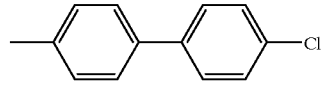 | CH$_3$ | |
| 3.88 | CH$_3$ | 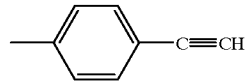 | CH$_3$ | |

TABLE 4

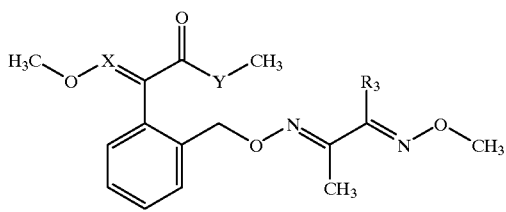

| Ex. No. | X | Y | R$_3$ | Physical data |
|---|---|---|---|---|
| 4.1 | CH | O | 4-C$_6$H$_4$—C≡C-2',4'-C$_6$H$_3$Cl$_2$ | M.p. 134–136° C. |
| 4.2 | CH | O | 4-C$_6$H$_4$—C≡C—C$_6$H$_5$ | |
| 4.3 | CH | O | 4-C$_6$H$_4$—C≡C-4'-C$_6$H$_4$(OCH$_3$) | |
| 4.4 | CH | O | 4-C$_6$H$_4$—C≡C-3',5'-C$_6$H$_3$(CF$_3$)$_2$ | M.p. 172–173° C. |
| 4.5 | CH | O | 4-C$_6$H$_4$—C≡C-3'-C$_6$H$_4$(CF$_3$) | |
| 4.6 | CH | O | 4-C$_6$H$_4$—C≡C-3'-CO—C$_6$H$_4$(CF$_3$) | M.p. 129–130° C. |
| 4.7 | CH | O | 4-C$_6$H$_4$—C≡C—CO—C$_6$H$_5$ | |
| 4.8 | CH | O | 4-C$_6$H$_4$—C≡C—CO-3'-C$_6$H$_4$Cl | M.p. 136–138° C. |

TABLE 4-continued

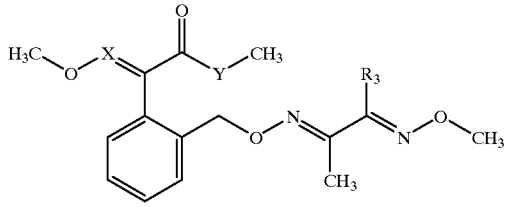

| Ex. No. | X | Y | R₃ | Physical data |
|---|---|---|---|---|
| 4.9 | CH | O | 4-C₆H₄—C≡C—C≡C-isoC₃H₇ | |
| 4.10 | CH | O | 4-C₆H₄—C≡C—C≡C—C(CH₃)₂—OH | Solid |
| 4.11 | CH | O | 4-C₆H₄—(C≡C)₂—C(CH₃)₂—OCOCH₃ | M.p. 135–138° C. |
| 4.12 | CH | O | 4-C₆H₄—C≡C—C(CH₃)₂—OH | Resin |
| 4.13 | CH | O | 4-C₆H₄—C≡C-2'-pyrazinyl | M.p. 156–158° C. |
| 4.14 | CH | O | 4-C₆H₄—C≡C-3'-pyridyl | M.p. 106–108° C. |
| 4.15 | CH | O | 4-C₆H₄—C≡C—CO-3'-pyridyl | M.p. 182–185° C. |
| 4.16 | CH | O | 4-C₆H₄—C≡C-2'-pyridyl | |
| 4.17 | CH | O | 4-C₆H₄—C≡C-4'-pyridyl | |
| 4.18 | N | O | 4-C₆H₄—C≡C—C₆H₅ | |
| 4.19 | N | O | 4-C₆H₄—C≡C-3'-C₆H₄(CF₃) | M.p. 150–152° C. |
| 4.20 | N | O | 4-C₆H₄—C≡C-4'-C₆H₄(CF₃) | |
| 4.21 | N | O | 4-C₆H₄—C≡C-4'-C₆H₄Cl | |
| 4.22 | N | O | 4-C₆H₄—C≡C—CO-3'-C₆H₄Cl | M.p. 152–154° C. |
| 4.23 | N | O | 4-C₆H₄—C≡C—CH₂—OH | |
| 4.24 | N | O | 4-C₆H₄—C≡C-3'-pyridyl | M.p. 123–124° C. |
| 4.25 | N | O | 4-C₆H₄—C≡C-2'-pyridyl | |
| 4.26 | N | O | 4-C₆H₄—C≡C-4'-pyridyl | |
| 4.27 | N | O | 4-C₆H₄—C≡C-2'-pyrazinyl | M.p. 136–138° C. |
| 4.28 | N | O | 4-C₆H₄—C≡C-2'-pyrimidinyl | |
| 4.29 | N | O | 4-C₆H₄—C≡C-4'-pyrimidinyl | |
| 4.30 | N | O | 4-C₆H₄—C≡C-5'-pyrimidinyl | |
| 4.31 | N | O | 4-C₆H₄—C≡C—I | |
| 4.32 | N | O | 4-C₆H₄—C≡C—C(CH₃)₂—OH | |
| 4.33 | N | O | 4-C₆H₄—C≡C—CH₃ | |
| 4.34 | N | O | 4-C₆H₄—C≡C—Br | |
| 4.35 | CH | O | 4-C₆H₄—C≡C—Br | |
| 4.36 | N | NH | 4-C₆H₄—C≡C—C₆H₅ | |
| 4.37 | N | NH | 4-C₆H₄—C≡C-4'-C₆H₄Br | |
| 4.38 | N | NH | 4-C₆H₄—C≡C-3',4',5'-C₆H₂(OCH₃)₃ | |
| 4.39 | N | NH | 4-C₆H₄—C≡C-3',5'-C₆H₃(CH₃)₂ | |
| 4.40 | N | NH | 4-C₆H₄—C≡C-2'-Cl-4'-CN—C₆H₃ | |
| 4.41 | N | NH | 4-C₆H₄—C≡C—C(CH₃)₂—OH | |
| 4.42 | N | NH | 4-C₆H₄—C≡C-iso-C₃H₇ | |
| 4.43 | N | NH | 4-C₆H₄—C≡C—I | |
| 4.44 | N | NH | 4-C₆H₄—C≡C-2'-pyridyl | |
| 4.45 | N | NH | 4-C₆H₄—C≡C-3'-pyridyl | |
| 4.46 | N | NH | 4-C₆H₄—C≡C-4'-pyridyl | |
| 4.47 | N | NH | 4-C₆H₄—C≡C-2'-pyrazinyl | |
| 4.48 | N | NH | 4-C₆H₄—C≡C-2'-pyrimidinyl | |
| 4.49 | N | NH | 4-C₆H₄—C≡C-5'-pyrimidinyl | |
| 4.50 | N | NH | 4-C₆H₄—C≡C-4'-pyrimidinyl | |
| 4.51 | N | NH | 4-C₆H₄—C≡C-2'-thiazolyl | |
| 4.52 | N | NH | 4-C₆H₄—C≡C-2'-oxazolyl | |
| 4.53 | CH | O | 4-C₆H₄—C≡C-2'-thienyl | |
| 4.54 | CH | O | 4-C₆H₄—C≡C-3'-thienyl | |
| 4.55 | N | NH | 4-C₆H₄—C≡C—Br | |
| 4.56 | CH | O | 4-C₆H₄—C≡C—CH₃ | |
| 4.57 | CH | O | 4-C₆H₄—C≡C—C₂H₅ | |
| 4.58 | CH | O | 2-C₆H₄—C≡CH | |
| 4.59 | CH | O | 3-C₆H₄—C≡CH | |
| 4.60 | N | O | 2-C₆H₄—C≡CH | |
| 4.61 | N | O | 3-C₆H₄—C≡C—CH₃ | |
| 4.62 | N | NH | 2-C₆H₄—C≡C—Br | |
| 4.63 | N | NH | 3-C₆H₄—C≡CH | |
| 4.64 | CH | O | 2-C₆H₄—C≡C—C(CH₃)₂—OH | |
| 4.65 | N | O | 3-C₆H₄—C≡C—C(CH₃)₂—OH | |
| 4.66 | CH | O | 4-C₆H₄—C≡C—CF₃ | |
| 4.67 | N | O | 4-C₆H₄—C≡C—CF₃ | |
| 4.68 | N | NH | 4-C₆H₄—C≡C—CF₃ | |
| 4.69 | CH | O | 4-C₆H₄—C≡C—COOC₂H₅ | |
| 4.70 | N | O | 4-C₆H₄—C≡C—COOC₂H₅ | |
| 4.71 | N | NH | 4-C₆H₄—C≡C—COOCH₃ | |
| 4.72 | CH | O | 4-C₆H₄—C≡C—CH(CH₃)=CH₂ | |
| 4.73 | N | O | 4-C₆H₄—C≡C—CH(CH₃)=CH₂ | |

TABLE 4-continued

[Structure: H3C-O-N=C(C6H4-)-C(=O)-Y-CH3 with the phenyl ring bearing an ortho -CH2-O-N=C(CH3)-C(R3)=N-OCH3 group; X replaces the N on the left oxime]

| Ex. No. | X | Y | R3 | Physical data |
|---|---|---|---|---|
| 4.74 | N | NH | 4-C6H4—C≡C—CH(CH3)=CH2 | |
| 4.75 | CH | O | 4-C6H4—C≡C—CH(CH3)=CH—CH2Cl | |
| 4.76 | N | O | 4-C6H4—C≡C—CH(CH3)=CH—CH2Cl | |
| 4.77 | N | NH | 4-C6H4—C≡C—CH(CH3)=CH—CH2Cl | |
| 4.78 | CH | O | 4-C6H4—C≡C-2'-pyrimidinyl | |
| 4.79 | CH | O | 4-C6H4—C≡C-4'-pyrimidinyl | |
| 4.80 | CH | O | 4-C6H4—C≡C-5'-pyrimidinyl | Oil |
| 4.81 | CH | O | 4-C6H4—C≡C—COO—CH2-2',2',-Cl2-cyclopropyl | |
| 4.82 | CH | O | 4-C6H4—C≡C—C(CH3)2—O—CH3 | |
| 4.83 | N | O | 4-C6H4—C≡C—C(CH3)2—O—CH3 | |
| 4.84 | N | NH | 4-C6H4—C≡C—C(CH3)2—O—CH3 | |
| 4.85 | N | O | 4-C6H4—C≡C—C(CH3)2—OH | |
| 4.86 | N | O | 4-C6H4—C≡C—CH2—O—CH3 | |
| 4.87 | CH | O | 3-C6H4—C≡C—C(CH3)2—O—CH3 | |
| 4.88 | CH | O | 2-C6H4—C≡C—C(CH3)2—O—CH3 | |
| 4.89 | CH | O | —4-C6H4—C≡C—(4-chloro-3-cyano-isothiazol-5-yl) | |
| 4.90 | N | O | —4-C6H4—C≡C—(4-chloro-3-cyano-isothiazol-5-yl) | |
| 4.91 | N | NH | —4-C6H4—C≡C—(4-chloro-3-cyano-isothiazol-5-yl) | |
| 4.92 | CH | O | 4-C6H4—C≡C-nC4H9 | |
| 4.93 | N | O | 4-C6H4—C≡C-nC4H9 | |
| 4.94 | N | O | 3-C6H4—C≡C-nC4H9 | |
| 4.95 | N | O | 2-C6H4—C≡C-nC4H9 | |
| 4.96 | CH | O | 2-C6H4—C≡C-nC4H9 | |
| 4.97 | CH | O | —4-C6H4—C≡C—COON(CH3)(OCH3) | |
| 4.98 | N | O | —4-C6H4—C≡C—COON(CH3)(OCH3) | |
| 4.99 | CH | O | 4-C6H4—C≡C—CH(CH3)=CHCH2—OCH3 | |
| 4.100 | N | O | 4-C6H4—C≡C—CH(CH3)=CHCH2—OCH3 | |
| 1.101 | N | NH | 4-C6H4—C≡C—CH(CH3)=CHCH2—OCH3 | |
| 4.102 | CH | O | 4-C6H4—C≡C-(4'-methoxy-6'-chlorotriazin-2'-yl) | |
| 4.103 | N | O | 4-C6H4—C≡C-(4'-methoxy-6'-chlorotriazin-2'-yl) | |
| 4.104 | CH | O | 4-C6H4—C≡C-3'-pyridazinyl | |
| 4.105 | N | O | 4-C6H4—C≡C-3'-pyridazinyl | |

TABLE 4a

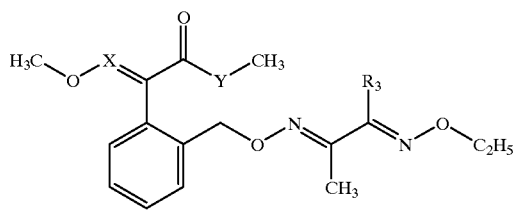

The compounds Nos. 4a.1 to 4a.105 in this table correspond in the same sequence to the structural details for X, Y and R₃ of Table 4 containing the compounds 4.1 to 4.105. Besides fungicidal action, compounds of Table 4a particularly display insecticidal and acaricidal action.

PREPARATION OF INTERMEDIATES

Example Z-1

Preparation of the starting material of the formula

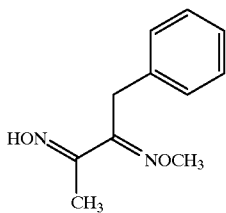

a) 2.6 g of a 60% sodium hydride dispersion are washed with hexane and treated with 50 ml of N,N-dimethylformamide. 8.9 g of 3-hydroximino-4-phenyl-2-butanone (prepared according to A. F. Ferris; J. Org. Chem. 24, 1726 (1959)) are added in portions to this suspension. After the evolution of hydrogen has ended, the mixture is cooled in an ice-bath and 3.4 ml of methyl iodide are added dropwise. After stirring at room temperature for 1 hour, the mixture is poured onto ice-water and extracted with ethyl acetate. After concentrating the organic phase on a rotary evaporator, the residue is chromatographed on silica gel using hexane. 3-Methoximino-4-phenyl-2-butanone is obtained as a colourless oil.

b) 5.7 g of the oil obtained above and 2.8 g of hydroxylamine hydrochloride in 30 ml of pyridine are stirred at 40° C. for 5 hours. The mixture is poured onto ice-water and the crystals formed overnight from the precipitated oil are filtered off. The starting material is obtained in the form of white crystals of m.p. 94–95° C. (Compound No. 5.1).

Example Z-2

Preparation of the starting material of the formula

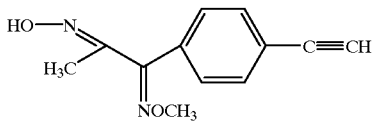

2-Hydroximino-3-(4-ethynylphenyl)-3-methoximinopropane a) 26 ml of 3-methyl-1-butyn-3-ol and 0.3 g of copper(I) iodide and 0.8 g of Pd(TPP)₂Cl₂ are added with stirring to a solution of 51.5 g of 4-bromopropiophenone in 600 ml of triethylamine. After warming to about 65° C., the reaction mixture is stirred for 1.5 hours, then the residue is filtered off with suction and the filtrate is evaporated. The oil which remains is chromatographed on silica gel (eluent: diethyl ether). 52 g of 4-(3-hydroxy-3-methyl-1-butynyl)propiophenone are obtained; m.p. 56–58° C.

b) 3 g of NaOH powder are added to a solution of 44 g of the intermediate obtained in a) in 500 ml of toluene and the reaction mixture is stirred at 100° C. for 5 hours. It is then evaporated and the oily residue which remains is chromatographed on silica gel (ethyl acetate/hexane 1:5). 26.7 g of 4-ethynylpropiophenone are obtained; m.p. 65–67° C.

c) HCl gas is passed into a solution of 94 g of 4-ethynylpropiophenone in 1200 ml of dioxane for one minute. 90 g of isopentyl nitrite are then added dropwise with stirring during the course of a few minutes. The reaction mixture is stirred at room temperature for 2 hours. After the addition of 10 ml of triethylamine, solid material is filtered off with suction and the filtrate is evaporated. The oily residue is chromatographed on silica gel (ethyl acetate/hexane 2:7). 89 g of 2-hydroximino3-(4-ethnynylphenyl)propan-3-one are obtained; m.p. 131–132° C.

d) 8 g of methoxyamine hydrochloride are added to a solution of 15 g of the intermediate obtained according to c) in 100 ml of pyridine. After stirring at 100° C. for 2.5 hours, the reaction mixture is evaporated and extracted twice by shaking with 200 ml of diethyl ether each time. The combined ether phase is washed twice with 100 ml of water each time, concentrated and chromatographed on silica gel (hexane/diisopropyl ether 3:1). 8.35 g of crystals of the title compound are obtained; m.p. 149–151° C. (Compound No. 5.88). In addition, 5.8 g of the Z isomer are obtained; m.p. 111–113° C.

Example Z-3

Preparation of 2-hydroximino-3-(4-ethynylphenyl)-3-methoximinopropane a) 0.35 g (0.5 mmol) Pd[TPP]₂Cl₂ and 0.12 g (=0.6 mmol) of copper(I) iodide and, with stirring in the course of a few minutes, 10.7 g (=0.13 mmol) of 1-methyl-3-butyn-1-ol are added to a solution of 21.3 g (=0.1 mol) of 4-bromophenylacetone in 250 ml of triethylamine. The mixture is warmed to 55° C. and the temperature is allowed slowly to rise to 80° C. during the course of 4 hours. After cooling, the mixture is filtered and the filtrate is concentrated. The oil which remains is chromatographed on silica gel. 17.4 g (90.3% of theory) of 4-(3-hydroxy-3-methyl-1-butynyl)phenylacetone are obtained; m.p. 67–69° C.

b) 11 g (=0.2 mol) of KOH are added to a solution of 41 g (=0.19 mol) of the intermediate obtained in a) in 800 ml of toluene and the reaction mixture is stirred at 85–96° C. for 35 min. After filtering, the filtrate is evaporated and the oily residue is chromatographed on silica gel. 19.6 g (=65.2% of theory) of 4-ethynylphenylacetone are obtained; H-NMR (CDCl₃; 250 MHz): 2.18(s); 3.08(s); 3.71(s); 7.17(m); 7.47 (m).

c) 8 g of Na (=0.35 mol) are dissolved at room temperature in 300 ml of methanol. 44 g (=0.28 mol) of 4-ethynylphenylacetone are added to this solution and 34.2 g (0.29 mol) of isopentyl nitrite are allowed to run in dropwise in the course of a few minutes, during which the reaction mixture warms to about 32° C. It is stirred for 1.5 hours, then evaporated. 48.5 g (=93.2% of theory) of 1-hydroximino-1-(4'-ethynylphenyl)propan-2-one are obtained; H-NMR: 2.47(s); 3.07(s); 7.20(m); 7.48(m); 8.01 (s).

d) 72.8 g (=0.51 mol) of methyl iodide and 71.6 g (=0.52 mol) of K$_2$CO$_3$ are added to a solution of 59.7 g (=0.32 mol) of the product obtained in c) in 500 ml of acetonitrile. The mixture is stirred at 40–42° C. for 19 hours, concentrated to a volume of about 200 ml and cooled, and the inorganic constituent is filtered off. The filtrate is concentrated further. 60.7 g (=94.6% of theory) of 1-methoximino-1-(4'-ethynylphenyl)propan-2-one remain as an oil. H-NMR: 2.53 (s); 3.10(s); 4.07(s); 7.27(m); 7.52(m).

e) 60.7 g (=0.3 mol) of 1-methoximino-1-(4'-ethynylphenyl)propan-2-one are dissolved in 600 ml of ethanol and treated with 22 g (=0.315 mol) of hydroxylamine hydrochloride and 29.4 g (=0.372 mol) of pyridine. After stirring at room temperature for 15 hours, the solution is evaporated and filtered, and the concentrated oily filtrate is purified on silica gel. 55.3 g (=84.7% of theory) of [E]-2-hydroximino-3-(4-ethynylphenyl)-3-methoximinopropane are obtained. H-NMR: 1.98(s); 2.90 (s); 3.73(s); 6.98(m); 7.32(m); 8.07(s). M.p. 150–151° C. (Compound No. 5.88). The corresponding [Z] isomer is formed in only very small amounts by this method.

TABLE 5

(Intermediates)

(IVa)

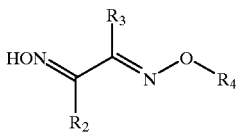

| Ex. No. | R$_2$ | R$_3$ | R$_4$ | M.p. or $^1$H—NMR or R$_2$ |
|---|---|---|---|---|
| 5.1 | CH$_3$ | 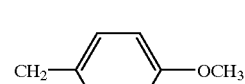 | CH$_3$ | 94–95° C. |
| 5.2 | CH$_3$ | 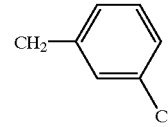 | CH$_3$ | 79–80° C. |
| 5.3 | CH$_3$ | 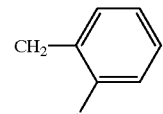 | CH$_3$ | |
| 5.4 | CH$_3$ | 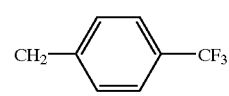 | CH$_3$ | |
| 5.5 | CH$_3$ | 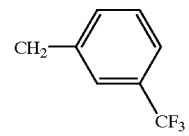 | CH$_3$ | |
| 5.6 | CH$_3$ | 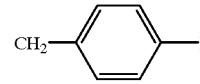 | CH$_3$ | |
| 5.7 | CH$_3$ | 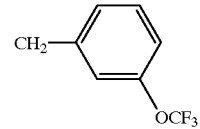 | CH$_3$ | |
| 5.8 | CH$_3$ | | CH$_3$ | |

TABLE 5-continued (Intermediates)

(IVa)

Structure: HON=C(R2)-C(R3)=N-O-R4

| Ex. No. | R₂ | R₃ | R₄ | M.p. or ¹H—NMR or R₂ |
|---|---|---|---|---|
| 5.9 | CH₃ | CH₂-(4-CN-C₆H₄) | CH₃ | |
| 5.10 | CH₃ | CH₂-(4-NO₂-C₆H₄) | CH₃ | |
| 5.11 | CH₃ | CH₂-(3-SCH₃-C₆H₄) | CH₃ | |
| 5.12 | CH₃ | CH₂-(2-pyridyl) | CH₃ | |
| 5.13 | CH₃ | CH₂-(3-pyridyl) | CH₃ | |
| 5.14 | CH₃ | CH₂-(4-pyridyl) | CH₃ | |
| 5.15 | H | CH₂-C₆H₅ | CH₃ | |
| 5.16 | cyclopropyl | CH₂-(4-Cl-C₆H₄) | CH₃ | |
| 5.17 | CH₃CH₂ | CH₂-(4-OCF₃-C₆H₄) | CH₃ | |
| 5.18 | CH₃ | CH₂-(3-F-C₆H₄) | CH₃CH₂ | |
| 5.19 | CH₃ | CH₂-C₆H₅ | t-Butyl | |

TABLE 5-continued (Intermediates)

$$\text{HON}=\underset{R_2}{\overset{R_3}{C}}-\underset{}{\overset{}{C}}=N-O-R_4 \quad \text{(IVa)}$$

| Ex. No. | R$_2$ | R$_3$ | R$_4$ | M.p. or $^1$H—NMR or R$_2$ |
|---|---|---|---|---|
| 5.20 | CH$_3$ | CH$_2$—C$_6$H$_5$ | HC≡C—CH$_2$ | |
| 5.21 | CH$_3$ | CH$_2$—C$_6$H$_5$ | cyclopropyl-CH$_2$ | |
| 5.22 | CH$_3$ | CH$_2$—C$_6$H$_5$ | H$_2$C=C(Cl)CH$_2$ | |
| 5.23 | CH$_3$ | CH$_2$—C$_6$H$_5$ | F$_3$CCH$_2$ | |
| 5.24 | CH$_3$ | CH$_2$—C$_6$H$_5$ | FCH$_2$CH$_2$ | |
| 5.25 | CH$_3$ | CH$_2$—C$_6$H$_5$ | F$_3$CCH$_2$CH$_2$CH$_2$ | |
| 5.26 | CH$_3$ | CH$_2$—C$_6$H$_5$ | 2,2-dichlorocyclopropyl-CH$_2$ | |
| 5.27 | CH$_3$ | CH$_2$-(2-naphthyl) | CH$_3$ | |
| 5.28 | CH$_3$ | O—C$_6$H$_5$ | CH$_3$ | White crystals |
| 5.29 | CH$_3$ | O—C$_6$H$_4$—Cl (4-) | CH$_3$ | |
| 5.30 | CH$_3$ | O—C$_6$H$_4$—Cl (3-) | CH$_3$ | |

TABLE 5-continued (Intermediates)

(IVa)

$$\text{HON} = \overset{R_3}{\underset{R_2}{C}} - C = N - O - R_4$$

| Ex. No. | $R_2$ | $R_3$ | $R_4$ | M.p. or $^1$H—NMR or $R_2$ |
|---|---|---|---|---|
| 5.31 | $CH_3$ | O—(2-Cl-C$_6$H$_4$) | $CH_3$ | |
| 5.32 | $CH_3$ | O—(4-CF$_3$-C$_6$H$_4$) | $CH_3$ | |
| 5.33 | $CH_3$ | O—(3-CF$_3$-C$_6$H$_4$) | $CH_3$ | |
| 5.34 | $CH_3$ | O—(4-SCH$_3$-C$_6$H$_4$) | $CH_3$ | |
| 5.35 | $CH_3$ | O—(4-S(O)CH$_3$-C$_6$H$_4$) | $CH_3$ | |
| 5.36 | $CH_3$ | O—(4-SO$_2$CH$_3$-C$_6$H$_4$) | $CH_3$ | |
| 5.37 | $CH_3$ | O—(4-S(CH$_2$)$_3$CH$_3$-C$_6$H$_4$) | $CH_3$ | |
| 5.38 | $CH_3$ | O—(4-S(O)(CH$_2$)$_3$CH$_3$-C$_6$H$_4$) | $CH_3$ | |
| 5.39 | $CH_3$ | O—(4-SO$_2$(CH$_2$)$_3$CH$_3$-C$_6$H$_4$) | $CH_3$ | |
| 5.40 | $CH_3$ | O-(1-naphthyl) | $CH_3$ | |

TABLE 5-continued (Intermediates) (IVa)

$$\text{HON}=\underset{R_2}{\overset{R_3}{C}}-\underset{}{\overset{}{C}}=N-O-R_4$$

| Ex. No. | $R_2$ | $R_3$ | $R_4$ | M.p. or $^1$H—NMR or $R_2$ |
|---|---|---|---|---|
| 5.41 | $CH_3$ | 2-naphthyloxy | $CH_3$ | |
| 5.42 | $CH_3$ | 2-pyridyloxy | $CH_3$ | |
| 5.43 | $CH_3$ | 3-pyridyloxy | $CH_3$ | |
| 5.44 | $CH_3$ | 4-pyridyloxy | $CH_3$ | |
| 5.45 | $CH_3$ | 2-pyrimidinyloxy | $CH_3$ | |
| 5.46 | $CH_3$ | 2-quinolinyloxy | $CH_3$ | |
| 5.47 | $CH_3$ | 4-quinolinyloxy | $CH_3$ | |
| 5.48 | $CH_3$ | 5-quinolinyloxy | $CH_3$ | |
| 5.49 | $CH_3$ | 6-quinolinyloxy | $CH_3$ | |

TABLE 5-continued (Intermediates)

(IVa)

| Ex. No. | R$_2$ | R$_3$ | R$_4$ | M.p. or $^1$H—NMR or R$_2$ |
|---|---|---|---|---|
| 5.50 | CH$_3$ | 8-quinolinyloxy | CH$_3$ | |
| 5.51 | CH$_3$ | 1-isoquinolinyloxy | CH$_3$ | |
| 5.52 | CH$_3$ | 5-isoquinolinyloxy | CH$_3$ | |
| 5.53 | CH$_3$ | 4-quinazolinyloxy | CH$_3$ | |
| 5.54 | CH$_3$ | 2-quinoxalinyloxy | CH$_3$ | |
| 5.55 | CH$_3$ | phenylthio | CH$_3$ | 115–116° C. |
| 5.56 | CH$_3$ | 4-methylphenylthio | CH$_3$ | 113–114° C. |
| 5.57 | H | phenylthio | CH$_3$ | |
| 5.58 | cyclopropyl | phenylthio | CH$_3$ | |

TABLE 5-continued
(Intermediates)
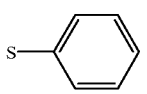
(IVa)
| Ex. No. | R$_2$ | R$_3$ | R$_4$ | M.p. or $^1$H—NMR or R$_2$ |
|---|---|---|---|---|
| 5.59 | CH$_3$CH$_2$CH$_2$ | 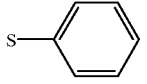 | CH$_3$ | |
| 5.60 | CH$_3$(CH$_2$)$_3$ | 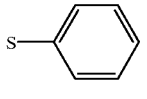 | CH$_3$ | |
| 5.61 | (CH$_3$)$_2$CH | 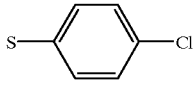 | CH$_3$ | |
| 5.62 | CH$_3$ | 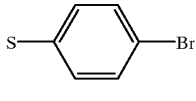 | CH$_3$ | |
| 5.63 | CH$_3$ | 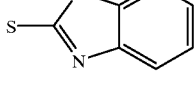 | CH$_3$ | |
| 5.64 | CH$_3$ | 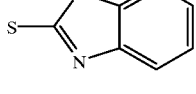 | CH$_3$ | |
| 5.65 | CH$_3$ | 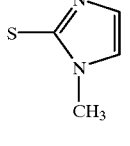 | CH$_3$ | |
| 5.66 | CH$_3$ | 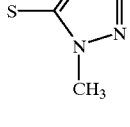 | CH$_3$ | |
| 5.67 | CH$_3$ | 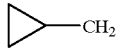 | CH$_3$ | |
| 5.68 | CH$_3$ | SCH$_3$ | CH$_3$ | White crystals |
| 5.69 | CH$_3$ | SCH$_2$CH$_3$ | CH$_3$ | |
| 5.70 | CH$_3$ | SCH$_2$CH$_2$CH$_3$ | CH$_3$ | |
| 5.71 | CH$_3$ | S(CH$_2$)$_5$CH$_3$ | CH$_3$ | |
| 5.72 | CH$_3$ | SCH$_3$ | CH$_3$CH$_2$ | |
| 5.73 | CH$_3$ | SCH$_3$ | ▷—CH$_2$ | |
| 5.74 | CH$_3$ | SCH$_3$ | F$_3$CCH$_2$ | |
| 5.75 | CH$_3$ | SCH$_3$ | FCH$_2$CH$_2$ | |

TABLE 5-continued (Intermediates)

$$\text{HON}=\underset{R_2}{\overset{R_3}{C}}-\underset{}{\overset{}{C}}=N-O-R_4 \quad \text{(IVa)}$$

| Ex. No. | $R_2$ | $R_3$ | $R_4$ | M.p. or $^1$H—NMR or $R_2$ |
|---|---|---|---|---|
| 5.76 | $CH_3$ | $SCH_3$ | $F_3CCH_2CH_2CH_2$ | |
| 5.77 | $CH_3$ | $OCH_3$ | $CH_3$ | |
| 5.78 | $CH_3$ | $OCH_2CH_3$ | $CH_3$ | |
| 5.79 | $CH_3$ | $OCH_2CF_3$ | $CH_3$ | |
| 5.80 | $CH_3$ | $OCH_2CH_2CH_3$ | $CH_3$ | |
| 5.81 | $CH_3$ | $OCH_2CH_2Cl$ | $CH_3$ | |
| 5.82 | $CH_3$ | $OCH_2CH_2CH(CH_3)_2$ | $CH_3$ | |
| 5.83 | $CH_3$ | $OCH_2C(CH_3)_3$ | $CH_3$ | |
| 5.84 | $CH_3$ | $O(CH_2)_5CH_3$ | $CH_3$ | |
| 5.85 | $CH_3$ | 4-biphenyl | $CH_3$ | |
| 5.86 | $CH_3$ | 3-biphenyl | $CH_3$ | |
| 5.87 | $CH_3$ | 4'-chloro-4-biphenyl | $CH_3$ | |
| 5.88 | $CH_3$ | 4-(ethynyl)phenyl | $CH_3$ | [E] 150–151° C. [Z] 111–113° C. |

2. FORMULATION EXAMPLES FOR ACTIVE INGREDIENTS OF THE FORMULA I (%= PERCENT BY WEIGHT)

2.1. Wettable powder

| | a) | b) | c) |
|---|---|---|---|
| Active ingredient from Table 1-4a | 25% | 50% | 75% |
| Sodium lignosulfonate | 5% | 5% | — |
| Sodium laurylsulfate | 3% | — | 5% |
| Sodium diisobutylnaphthalenesulfonate | — | 6% | 10% |
| Octylphenol polyethylene glycol ether (7–8 mol of ethylene oxide) | — | 2% | — |
| Highly disperse silicic acid | 5% | 10% | 10% |
| Kaolin | 62% | 27% | — |

The active ingredient is well mixed with the additives and well ground in a suitable mill. Wettable powders are obtained which can be diluted with water to give suspensions of any desired concentration.

2.2. Emulsion concentrate

| | |
|---|---|
| Active ingredient from Table 1-4a | 10% |
| Octylphenol polyethylene glycol ether (4–5 mol of ethylene oxide) | 3% |
| Calcium dodecylbenzenesulfonate | 3% |
| Cyclohexanone | 34% |
| Xylene mixture | 50% |

Emulsions of any desired dilution can be prepared from this concentrate by diluting with water.

2.3. Dusting composition

| | a) | b) |
|---|---|---|
| Active ingredient from Table 1-4a | 5% | 8% |
| Talc | 95% | — |
| Kaolin | — | 92% |

Ready-to-use dusting compositions are obtained by grinding the active ingredient mixed with the carrier in a suitable mill.

| 2.4. Extruder granules | |
| --- | --- |
| Active ingredient from Table 1-4a | 10% |
| Sodium lignosulfonate | 2% |
| Carboxymethylcellulose | 1% |
| Kaolin | 87% |

The active ingredient is mixed with the additives, ground and moistened with water. This mixture is extruded and then dried in a stream of air.

| 2.5. Coated granules | |
| --- | --- |
| Active ingredient from Table 1-4a | 3% |
| Polyethylene glycol (MW 200) | 3% |
| Kaolin | 94% |

(MW = molecular weight)

The finely ground active ingredient is uniformly applied to the kaolin moistened with polyethylene glycol in a mixer. Dust-free coated granules are obtained in this manner.

| 2.6. Suspension concentrate | |
| --- | --- |
| Active ingredient from Table 1-4a | 40% |
| Ethylene glycol | 10% |
| Nonylphenol polyethylene glycol ether (15 mol of ethylene oxide) | 6% |
| Sodium lignosulfonate | 10% |
| Carboxymethylcellulose | 1% |
| 37% aqueous formaldehyde solution | 0.2% |
| Silicone oil in the form of a 75% aqueous emulsion | 0.8% |
| Water | 32% |

The finely ground active ingredient is intimately mixed with the additives. A suspension concentrate is thus obtained, from which suspensions of any desired dilution can be prepared by diluting with water.

3. BIOLOGICAL EXAMPLES

Example B-1
Action Against *Phytophthora infestans* on Tomatoes
a) Curative Action After growing for three weeks, tomato plants of the variety "Roter Gnom" are sprayed with a zoospore suspension of the fungus and incubated in a cabin at 18 to 20° and saturated atmospheric humidity. Humidification is interrupted after 24 hours. After the plants have dried off, they are sprayed with a liquor which contains the active substance formulated as a wettable powder in a concentration of 200 ppm. After the spray coating has dried on, the plants are again placed in the humidified cabin for 4 days. The number and size of the typical leaf spots which have appeared after this time are the evaluation scale for the efficacy of the substances tested.

b) Preventive-systemic Action

The active substance formulated as a wettable powder is added at a concentration of 60 ppm (based on the soil volume) to the soil surface of three week-old potted tomato plants of the variety "Roter Gnom". After a waiting time of three days, the underside of the leaf of the plants is sprayed with a zoospore suspension of *Phytophthora infestans*. They are then kept for 5 days in a spray cabin at 18 to 20° C. and saturated atmospheric humidity. After this time, typical leaf spots are formed, whose number and size are used to assess the efficacy of the substances tested.

While untreated, but infected control plants exhibit 100% attack, the attack in one of the two tests is suppressed to 10% or less by the active ingredients of the formula I according to one of Tables 1 to 3, in particular by the compounds Nos. 1.2, 1.6, 1.8, 1.28, 1.77, 1.85, 1.88, 2.2, 2.6, 2.8, 2.28, 2.55, 2.77, 2.85, 2.88, 3.1, 3.2, 3.6, 3.8, 3.28, 3.77, 3.85, 3.88. The vast majority of the compounds of Table 4 show an exceptionally good action (attack 10% to 0%).

Example B-2

Action Against *Plasmopara viticola* (Bert. and Curt.) (Berl. and DeToni) on Vines a) Residual-preventive Action Vine seedlings of the variety "Chasselas" are raised in a greenhouse. At the 10-leaf stage, 3 plants are sprayed with a liquor (200 ppm of active ingredient). After the spray coating has dried on, the plants are uniformly infected on the underside of the leaf with the spore suspension of the fungus. The plants are then kept in a humidity chamber for 8 days. After this time, clear symptoms of disease are seen on the control plants. The number and size of the infection sites on the treated plants are used as an evaluation scale for the efficacy of the substances tested.

b) Curative Action

Vine seedlings of the variety "Chasselas" are raised in a greenhouse and infected at the 10-leaf stage with a spore suspension of *Plasmopara viticola* on the underside of the leaf. After a stay of 24 hours in the humidity cabin, the plants are sprayed with an active ingredient liquor (200 ppm of active ingredient). The plants are then kept in the humidity cabin for a further 7 days. After this time, the symptoms of disease are seen on the control plants. The number and size of the infection sites on the treated plants are used as an evaluation scale for the efficacy of the substances tested.

In comparison with the control plants, the plants treated with the active ingredients of the formula I exhibit an attack of 20% or less. The preparations mentioned in Test B-1 suppress the attack to 10–0%.

Example B-3

Action Against *Pythium debaryanum* on Sugar Beet (*Beta vulgaris*)

a) Action After Soil Application

The fungus is cultured on sterile oats and admixed to an earth-sand mixture. The earth infected in this way is filled into flower pots and sown with sugar beet seeds. Immediately after sowing, the test preparations formulated as a wettable powder are poured over the earth as an aqueous suspension (20 ppm of active ingredient based on the soil volume). The pots are then placed in a greenhouse at 20–24° C. for 2–3 weeks. The earth is continuously kept uniformly moist by gentle spraying with water. In the evaluation of the tests, the emergence of the sugar beet plants and the proportion of healthy and diseased plants are determined.

b) Action After Seed Dressing

The fungus is cultured on sterile oats and admixed to an earth-sand mixture. The earth infected in this way is filled into flower pots and sown with sugar beet seeds which have been dressed with the test preparations formulated as a seed-dressing powder (1000 ppm of active ingredient based on the seed weight). The sown pots were placed in a greenhouse at 20–24° C. for 2–3 weeks. During the course of this, the earth is kept uniformly moist by gentle spraying with water.

In the evaluation, the emergence of the sugar beet plants and the proportion of healthy and diseased plants are determined.

After treatment with active ingredients of the formula I, over 80% of the plants emerge and have a healthy appearance. In the control pots, only plants with a sickly appearance which have emerged here and there are observed.

Example B-4
Residual-protective Action Against *Cercospora arachidicola* on Peanuts Peanut plants 10 to 15 cm high are sprayed with an aqueous spray liquor (0.02% active substance) until dripping wet and infected 48 hours later with a conidia suspension of the fungus. The plants are incubated at 21° and high atmospheric humidity for 72 hours and then placed in a greenhouse until the typical leaf spots occur. The evaluation of the action of the active substance is carried out 12 days after infection on the basis of the number and size of the leaf spots.

Active ingredients of the formula I cause a reduction of the leaf spots to less than about 10% of the leaf surface. In some cases, the disease is completely suppressed (0–5% attack).

Example B-5
Action Against *Puccinia graminis* on Wheat
a) Residual-protective Action Wheat plants are sprayed 6 days after sowing with an aqueous spray liquor (0.02% of active substance) until dripping wet and infected 24 hours later with a uredospore suspension of the fungus. After an incubation time of 48 hours (conditions: 95 to 100 per cent relative atmospheric humidity at 20° C.), the plants are placed in a greenhouse at 22°.

The evaluation of rust pustule development is carried out 12 days after infection.
b) Systemic Action 5 days after sowing, wheat plants are watered with an aqueous spray liquor (0.006% of active substance, based on the soil volume). Care is taken in the course of this that the spray liquor does not come into contact with above-ground plant parts. 48 hours later, the plants are infected with a uredospore suspension of the fungus. After an incubation time of 48 hours (conditions: 95 to 100 per cent relative atmospheric humidity at 20°), the plants are placed in a greenhouse at 22°. The evaluation of rust pustule development is carried out 12 days after infection.

Compounds of the formula I, e.g. Nos. 1.1, 1.2, 1.6, 1.8, 1.28, 1.55, 1.56, 1.68, 1.77, 1.85, 1.87, 1.88, 2.1, 2.2, 2.6, 2.8, 2.28, 2.55, 2.56, 2.68, 2.77, 2.85, 2.87, 2.88, 3.1, 3.2, 3.6, 3.8, 3.28, 3.55, 3.56, 3.68, 3.77, 3.85, 3.87, 3.88 and others cause a distinct reduction in fungal infestation, in some cases to 10–0%. Unusually persistent action is shown by compounds of subgroup 9) of the formula I, as are shown by way of example in Table 4, e.g. Nos. 4.12–4.17, 4.24–4.33 and others.

Example B-6
Action Against *Pyricularia oryzae* on Rice
a) Residual-protective Action After two weeks growth, rice plants are sprayed with an aqueous spray liquor (0.02% active substance) until dripping wet and infected 48 hours later with a conidia suspension of the fungus. Evaluaton of fungal infestation is carried out 5 days after infection, during which 95 to 100 per cent relative atmopsheric humidity and a temperature of 22° are maintained.

b) Systemic Action

An aqueous spray liquor (0.006% active substance, based on the soil volume) is poured onto rice plants 2 weeks old. Care is taken during the course of this that the spray liquor does not come into contact with above-ground plant parts. The pots are then filled with water to the extent that the lowest parts of the stalks of the rice plants stand in the water. After 96 hours, the plants are infected with a conidia suspension of the fungus and kept at 95 to 100 per cent relative atmopsheric humidity and a temperature of 24° C. for 5 days. Compounds of the formula I largely prevent the outbreak of the disease on the infected plants.

Example B-7
Residual-protective Action Against *Venturia inaequalis* on Apples Apple seedlings having fresh shoots 10 to 20 cm long are sprayed with a spray liquor (0.02% active substance) until dripping wet and infected 24 hours later with a conidia suspension of the fungus. The plants are incubated at 90 to 100 per cent relative atmospheric humidity for 5 days and placed in a greenhouse at 20 to 24° for a further 10 days. Evaluation of scab attack is carried out 15 days after infection. Compounds of the formula I from one of Tables 1 to 3 mainly display a persistent action against scab diseases. Even more distinct is the action of the compounds of subgroup 9).

Example B-8
Action Against *Erysiphe graminis* on Barley
a) Residual-protective Action Barley plants approximately 8 cm high are sprayed with an aqueous spray liquor (0.02% of active substance) until dripping wet and dusted with conidia of the fungus 3 to 4 days later. The infected plants are placed in a greenhouse at 22°. The evaluation of fungal infestation is carried out 10 days after infection.
b) Systemic Action An aqueous spray liquor (0.002% of active substance, based on the soil volume) is poured onto barley plants approximately 8 cm high. Care is taken during the course of this that the spray liquor does not come into contact with above-ground plant parts. 48 hours later, the plants are dusted with conidia of the fungus. The infected plants are placed in a greenhouse at 22°. Evaluation of fungal infestation is carried out 10 days after infection.

Compounds of the formula I, in particular the compounds Nos. 1.1, 1.2, 1.6, 1.8, 1.28, 1.55, 1.56, 1.68, 1.77, 1.85, 1.87, 1.88, 2.1, 2.2, 2.6, 2.8, 2.28, 2.55, 2.56, 2.68, 2.77, 2.85, 2.87, 2.88, 3.1, 3.2, 3.6, 3.8, 3.28, 3.55, 3.56, 3.68, 3.77, 3.85, 3.87, 3.88 and others, are generally able to suppress the attack by disease to less than 20%, in some cases even completely. Compounds of Table 4 are distinguished by particular efficacy, e.g. Nos. 4.13, 4.14, 4.24, 4,27 and others.

Example B-9
Action Against *Podosphaera leucotricha* on Apple Shoots
Residual-protective Action Apple seedlings having fresh shoots about 15 cm long are sprayed with a spray liquor (0.06% of active substance). After 24 hours, the treated plants are infected with a conidia suspension of the fungus and placed in a climatic chamber at 70% relative atmospheric humidity and 20° C. Evaluation of fungal infestation is carried out 12 days after infection. The attack by disease is suppressed to less than 20% by active compounds of the formula I. Control plants are attacked to 100%.

Example B-10
Action Against *Botrytis cinerea* on Pomaceous Fruits
Residual-protective Action Artifically injured apples are treated by adding a spray liquor (0.02 to active substance) dropwise to the injury sites. The treated fruits are then inoculated with a spore suspension of the fungus and incubated at high atmospheric humidity and about 20° C. for one week.

The fungicidal action of the test substance is derived from the number of injury sites beginning to rot.

Active ingredients of the formula I from Tables 1 to 3 are able completely to prevent the spread of rot in some cases. Particularly good action is shown by compounds of Table 4 as examples of the alkynylphenyl compounds of substance group 9.

Example B-11
Action Against *Helminthosporium gramineum*

Wheat grains are contaminated with a spore suspension of the fungus and allowed to dry. The contaminated grains are dressed with a suspension of the test substance (600 ppm of active ingredient based on the weight of the seeds). After two days, the grains are placed in suitable agar dishes and, after a further four days, the development of the fungal colonies around the grains is evaluated. The number and size of the fungal colonies are used to evaluate the test substance.

Compounds of the formula I in some cases exhibit a good action, i.e. inhibition of the fungal colonies.

Example B-12
Action Against *Colletotrichum lagenarium* on Cucumbers

After 2 weeks growth, cucumber plants are sprayed with a spray liquor (concentration 0.002%). After 2 days, the plants are infected with a spore suspension ($1.5 \times 10^5$ spores/ml) of the fungus and incubated at 23° C. and high atmospheric humidity for 36 hours. The incubation is then continued at normal atmospheric humidity and about 22–23° C. The fungal infestation which has set in is evaluated 8 days after infection. Untreated but infected control plants exhibit a fungal infestation of 100%.

Compounds of the formula I in some cases cause an almost complete inhibition of the attack by disease.

Example B-13
Action Against *Fusarium nivale* on Rye

Rye of the variety Tetrahell naturally infected with *Fusarium nivale* is dressed on a mixing roll with the fungicide to be tested, the following concentrations being used: 20 or 6 ppm of AS (based on the weight of the seed). The infected and treated rye is sown in October in the open with a sower on plots of length 3 m with 6 seed rows. 3 repetitions per concentration.

Until evaluation of attack, the experimental planting is cultivated under normal field conditions (preferably in a region with a uniform snow covering during the winter months).

To evaluate the phytotoxicity, the seed emergence is assessed in the autumn and the stand density/tillering is assessed in the spring.

To determine the active ingredient activity, the percentage proportion of Fusarium-attacked plants is counted in the early spring, immediately after the thaw. On treatment with a compound of the formula I, the number of attacked plants was less than 5%. The emerged plants had a healthy appearance.

Example B-14
Action Against *Septoria nodorum* on Wheat

Wheat plants are sprayed in the 3-leaf stage with a spray liquor (60 ppm of AS) prepared from wettable powder of the active substances.

After 24 hours, the treated plants are infected with a conidia suspension of the fungus. The plants are then incubated at 90–100% relative atmospheric humidity for 2 days and placed in a greenhouse at 20–24° C. for a further 10 days. 13 days after infection, the fungal infestation is assessed. Less than 1% of the wheat plants exhibited attack.

Example B-15
Action Against *Rhizoctonia solani* on Rice
Protective Local Soil Application Rice plants 10 days old are watered in a flower bowl with a suspension (spray liquor) prepared from formulated test substance, without contaminating above-ground plant parts. Infection is carried out three days later by placing one barley straw haulm infected with *Rhizoctonia solani* per pot between the rice plants. After incubation for 6 days in an air-conditioned room at a day temperature of 29° C. and a night temperature of 26° C. and 95% relative atmospheric humidity, the fungal infestation is assessed. Less than 5% of the rice plants exhibited attack. The plants had a healthy appearance.

Protective Local Foliar Application

Rice plants 12 days old are sprayed with a suspension prepared from formulated test substances. Infection is carried out one day later by placing one barley straw haulm infected with *Rhizoctonia solani* per pot between the rice plants. After incubation for 6 days in an air-conditioned room at a day temperature of 29° C. and a night temperature of 26° C. and 95% relative atmospheric humidity, assessment is carried out. Untreated but infected control plants exhibited a fungal infestation of 100%. Compounds of the formula I in some cases cause a complete inhibition of attack by disease.

INSECTICIDAL ACTION

Example B-16
Action Against *Heliothis virescens*

Young soya plants are sprayed with an aqueous emulsion spray liquor comprising 100 ppm of active ingredient, populated with 10 caterpillars of the first stage of *Heliothis virescens* after the spray coating has dried on and then added to a plastic container. From the comparisons of the number of dead caterpillars and the feeding damage between the treated and untreated plants, the percentage reduction of the population and the feeding damage (% efficacy) are determined 6 days later.

Compounds of the formula I show good efficacy in this test. Compounds of group 9 from Tables 4 and 4a, e.g. Compound 4.1, prove to be particularly active.

Example B-17
Action Against *Spodoptera littoralis*

Young soya plants are sprayed with an aqueous emulsion spray liquor comprising 100 ppm of active ingredient, populated with 10 caterpillars of the third stage of *Spodoptera littoralis* after the spray coating has dried on and then added to a plastic container. From the comparisons of the number of dead caterpillars and the feeding damage between the treated and untreated plants, the percentage reduction of the population and the percentage reduction of the feeding damage (% efficacy) is determined 3 days later.

Compounds of the tables show a good efficacy in this test, especially alkynylphenyl compounds of Tables 4 and 4a, such as compound 4.1.

Example B-22
Action Against *Plutella xylostella* Caterpillars

Young cabbage plants are sprayed with an aqueous emulsion spray liquor which comprises 100 ppm of the active ingredient. After the spray coating has dried on, the cabbage plants are populated with 10 caterpillars of the third stage of *Plutella xylostella* and added to a plastic container. Assessment is carried out 3 days later. From the comparison of the number of dead caterpillars and the feeding damage on the treated plants with that on the untreated plants, the percentage reduction of the population or the percentage reduction of the feeding damage (% efficacy) is determined.

Compounds from the tables show a good efficacy, particularly those from Tables 4 and 4a, e.g. Compound 4.1.

What is claimed is:

1. A compound of the formula

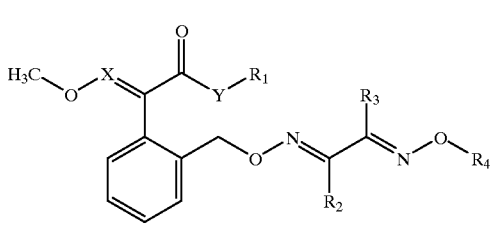

(I)

in which
a)
X is an N atom and
Y is an oxygen atom or NH, or
b)
X is CH and
Y is an oxygen atom,
$R_1$ is $C_1$–$C_4$alkyl;
$R_2$ is cyclopropyl;
$R_3$ is substituted or unsubstituted aryloxy, substituted or unsubstituted arylthio, substituted or unsubstituted heteroaryloxy, substituted or unsubstituted heteroarylthio, substituted or unsubstituted aralkyl, substituted or unsubstituted $C_2$–$C_4$alkynylphenyl, substituted or unsubstituted heteroarylmethyl; and
$R_4$ is $C_1$–$C_6$alkyl; $C_1$–$C_6$haloalkyl having 1 to 5 halogen atoms; $C_1$–$C_4$alkoxy-$C_1$–$C_2$alkyl; $C_2$–$C_6$alkenyl which is unsubstituted or substituted by 1 to 3 halogen atoms; $C_2$–$C_6$alkynyl; $C_3$–$C_6$cycloalkyl-$C_1$–$C_4$alkyl which is unsubstituted or substituted by 1 to 4 halogen atoms;
$R_2$ may also be methyl when $R_3$ is substituted or unsubstituted $C_2$–$C_4$alkynylphenyl.

2. The compound according to claim 1, in which
$R_3$ is substituted or unsubstituted phenoxy; or is unsubstituted or in each case halo-substituted pyridyloxy, pyrimidinyloxy, quinolyloxy, quinazolinyloxy or quinoxazolinyl; or an unsubstituted or $C_1$–$C_4$alkyl- or halogen-substituted benzothiazolylthio, benzoxazolylthio, imidazolylthio or tetrazolylthio radical; or a $C_2$–$C_4$alkynylphenyl, benzyl or naphthylmethyl, which is unsubstituted or substituted by 1 to 3 substituents selected from halogen, $C_1$–$C_4$alkyl, $C_1$–$C_4$alkoxy, $CF_3$ and CN;
$R_4$ is $C_1$–$C_4$alkyl; $C_1$–$C_4$haloalkyl; unsubstituted or halo-substituted $C_2$–$C_4$alkenyl; $C_3$–$C_4$alkynyl; unsubstituted or halo-substituted cyclopropylmethyl;
while X, Y, $R_1$ and $R_2$ are as defined for formula I.

3. The compound according to claim 1, in which:
X is CH or N
Y is oxygen,
$R_1$ is methyl or ethyl
$R_2$ is methyl or cyclopropyl, and in which
$R_3$ and $R_4$ are as defined for formula I.

4. The compound according to claim 1, in which:
X is nitrogen,
Y is NH,
$R_1$ is methyl, ethyl or isopropyl
$R_2$ is methyl or cyclopropyl, and in which
$R_3$ and $R_4$ are as defined for formula I.

5. The compound according to claim 1, in which:
$R_1$ is methyl
$R_2$ is methyl
$R_3$ is substituted or unsubstituted biphenyl or substituted or unsubstituted
$C_2$–$C_4$alkynylphenyl, while
X, Y and $R_4$ are as defined for formula I.

6. The compound according to claim 5, in which $R_4$ is methyl, ethyl or allyl, $R_3$ is an unsubstituted or substituted $C_2$–$C_4$alkynylphenyl group in which the possible substituent is located on the alkynyl group and is selected from $C_1$–$C_4$alkyl, $C_1$–$C_4$alkoxy, $C_1$–$C_4$haloalkyl (especially $CF_3$), $C_1$–$C_4$haloalkoxy (especially $OCF_3$), $C_1$–$C_4$alkylthio, halogen, nitro, cyano, $C_1$–$C_4$alkylsulfinyl, $C_1$–$C_4$alkylsulfonyl, unsubstituted or substituted phenyl (where the phenyl substituents are selected from $C_1$–$C_4$alkyl, $C_1$–$C_4$alkoxy, hydroxyl, $C_1$–$C_4$haloalkyl, $C_1$–$C_4$haloalkoxy, $C_1$–$C_4$alkylthio, halogen, nitro and cyano); $C_1$–$C_4$hydroxyalkyl, which can be O-acylated ($C_1$–$C_4$) or O-alkylated($C_1$–$C_4$); $C_1$–$C_5$alkoxycarbonyl; carbamoyl, N-($C_1$–$C_4$alkyl)carbamoyl; N,N-di($C_1$–$C_4$alkyl) carbamoyl; N-$C_1$–$C_4$alkyl-N-$C_1$–$C_4$alkoxycarbamoyl; unsubstituted or halogen-substituted cyclopropylmethoxycarbonyl, unsubstituted, $C_1$–$C_4$alkoxy-substituted or halogen-substituted $C_2$–$C_5$alkenyl, and a five- or six-membered heteroaryl ring which is unsubstituted or substituted by halogen, cyano, hydroxyl, and also alkyl, alkenyl, alkoxy, alkenyloxy or alkynyloxy each having not more than 4 carbon atoms.

7. The compound according to claim 6, in which $R_3$ is an unsubstituted or substituted ethynylphenyl group, the possible substituent on the ethynyl group being selected from $C_1$–$C_4$alkyl; $C_1$–$C_4$alkoxy; $C_1$–$C_2$haloalkyl; $C_1$–$C_2$haloalkoxy; fluorine, chlorine, bromine, iodine; nitro; cyano; phenyl which is unsubstituted or substituted up to three times (where the phenyl substituents are selected from $C_1$–$C_4$alkyl, $C_1$–$C_4$alkoxy, $C_1$–$C_4$haloalkyl, $C_1$–$C_4$haloalkoxy, hydroxyl, halogen, nitro, and cyano); $C_1$–$C_4$hydroxyalkyl, which can be O-alkylated($C_1$–$C_4$); $C_1$–$C_4$alkoxycarbonyl, N-methyl-N-methoxycarbamoyl and unsubstituted or substituted $C_2$–$C_5$alkenyl, whose possible substituents are selected from halogen and $C_1$–$C_2$alkoxy.

8. The compound according to claim 5, in which $R_3$ is a substituted ethynylphenyl group, the substituent on the ethynyl group being a five- or six-membered heteroaryl ring which is unsubstituted or substituted up to three times by halogen, cyano, $C_1$–$C_4$alkyl, $C_1$–$C_4$alkoxy or hydroxyl.

9. The compound according to claim 8, in which the heteroaryl ring is selected from pyridine, pyrimidine, pyrazine, pyridazine, triazine, (iso)thiazole, (iso)oxazole, pyrrole, pyrazole, imidazole, triazole and thiophene, and which is unsubstituted or substituted by up to three substituents selected from methyl, ethyl, isopropyl, CN, halogen, methoxy and hydroxyl.

10. The compound as claimed in claim 7, in which the substituent on the ethynyl group is selected from $C_1$–$C_4$alkyl; $C_1$–$C_4$alkoxy; $C_1$–$C_2$haloalkyl; $C_1$–$C_2$haloalkoxy; chlorine, bromine, iodine; nitro; cyano; $C_1$–$C_4$hydroxyalkyl, which can be O-$C_1$–$C_4$alkylated; $C_1$–$C_4$alkoxycarbonyl; N-methyl-N-methoxycarbamoyl and unsubstituted or substituted $C_2$–$C_5$alkenyl, whose possible substituents are selected from halogen and methoxy.

11. The compound according to claim 6, in which $R_3$ is an unsubstituted or substituted 3-4-$C_2$–$C_4$alkynyl)phenyl group.

X, Y and $R_4$ are as defined for formula I.

12. The compound according to claim 1, in which the X=C double bond has the E configuration.

13. The compound according to claim 5, in which $R_4$ is methyl and $R_3$ is 4-ethynylphenyl.

14. The compound according to claim 8, in which $R_4$ is methyl and $R_3$ is 4-(pyrazinylethynyl)phenyl.

15. The compound according to claim 8, in which $R_4$ is methyl and $R_3$ is 4-(pyridylethynyl)phenyl.

16. The compound according to claim 15, in which $R_3$ is 4-(3'-pyridylethynyl)phenyl.

17. The compound according to claim 8, in which $R_4$ is methyl and $R_3$ is 4-(5'-pyrimidinylethynyl)phenyl.

18. A process for the preparation of a compound of the formula I according to claim 1 by reaction of a compound of the formula II

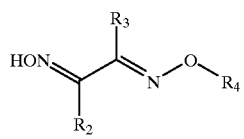

II with a compound of the formula III

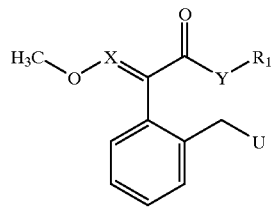

III where in X, Y and $R_1$ to $R_4$ are as defined for formula I.

19. A composition, which comprises a compound of the formula I according to claim 1 together with a suitable pesticidal carrier.

20. A method for the control or prevention of an attack on plants by microorganisms, Acarina or insects, which comprises applying an effective biocidal amount of the compound of the formula I according to claim 1 to the plants, to plant parts, plant propagation material, seeds or in the nutritive medium of the plant.

21. The method according to claim 20 the propagation material being treated.

22. The method according to claim 20 seed being treated.

23. The compound according to claim 1, in which at least one oximino double bond has the Z-form.

24. The compound according to claim 1, in which at least one oximino double bond has the E-form.

25. The compound according to claim 1, in which the X=C aliphatic double bond has the Z-form.

26. The compound according to claim 1, in which the X=C aliphatic double bond has the E-form.

27. The compound according to claim 1, which is a racemic mixture.

28. The compound according to claim 1, which is an optical isomer.

29. The compound according to claim 1, which is an E/Z-isomer mixture.

* * * * *